US010618944B2

(12) United States Patent
Peng et al.

(10) Patent No.: US 10,618,944 B2
(45) Date of Patent: Apr. 14, 2020

(54) TUMOR SUPPRESSOR SALL1 AS A THERAPEUTIC AGENT FOR TREATING CANCER

(71) Applicants: Saint Louis University, St. Louis, MO (US); U.S. Department of Veterans Affairs, Washington, DC (US)

(72) Inventors: Guangyong Peng, St. Louis, MO (US); Michael Rauchman, St. Louis, MO (US); Chunling Ma, St. Louis, MO (US); Fang Wang, St. Louis, MO (US)

(73) Assignees: Saint Louis University, St. Louis, MO (US); U.S. Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/553,953

(22) PCT Filed: Feb. 26, 2016

(86) PCT No.: PCT/US2016/019692
§ 371 (c)(1),
(2) Date: Aug. 25, 2017

(87) PCT Pub. No.: WO2016/138340
PCT Pub. Date: Sep. 1, 2016

(65) Prior Publication Data
US 2018/0244738 A1    Aug. 30, 2018

Related U.S. Application Data

(60) Provisional application No. 62/126,105, filed on Feb. 27, 2015.

(51) Int. Cl.
| | | |
|---|---|---|
| *C07K 14/47* | (2006.01) | |
| *A61K 38/17* | (2006.01) | |
| *A61K 45/06* | (2006.01) | |
| *A61K 9/51* | (2006.01) | |
| *A61P 35/00* | (2006.01) | |
| *C12N 15/86* | (2006.01) | |
| *A61K 38/00* | (2006.01) | |

(52) U.S. Cl.
CPC ........ *C07K 14/4703* (2013.01); *A61K 9/5123* (2013.01); *A61K 38/1709* (2013.01); *A61K 45/06* (2013.01); *A61P 35/00* (2018.01); *C12N 15/86* (2013.01); *A61K 38/00* (2013.01); *C12N 2830/008* (2013.01); *C12N 2840/007* (2013.01)

(58) Field of Classification Search
None
See application file for complete search history.

(56) References Cited

U.S. PATENT DOCUMENTS

| 7,157,079 B2* | 1/2007 | Nielsen | A61K 9/0019 424/93.2 |
|---|---|---|---|
| 2010/0081129 A1 | 4/2010 | Belouchi et al. | |
| 2010/0135958 A1 | 6/2010 | Hwu et al. | |
| 2012/0087901 A1 | 4/2012 | Nelson | |
| 2013/0315879 A1 | 11/2013 | Ma | |
| 2013/0315930 A1 | 11/2013 | Xing | |
| 2015/0057340 A1 | 2/2015 | Thess et al. | |

OTHER PUBLICATIONS

Netzer, et al. (2001) "SALL1, the gene mutated in Townes-Brocks syndrome, encodes a transcriptional repressor which interacts with TRF1/PIN2 and localizes to pericentromeric heterochromatin", Human Molecular Genetics, 10(26): 3017-24.*
https://www.cancer.gov/about-cancer/understanding/what-is-cancer, Author Unknown, no volume, no journal, Published by the National Cancer Institute, Bethesda, MD, USA, last updated Feb. 9, 2015, 9 pages as printed. (Year: 2015).*
Denner and Rauchman, "Mi-2/NuRD is required in renal progenitor cells during embryonic kidney development," *Develop. Biol.*, 375:105-116, 2013.
Guo et al., "Dysfunctional telomeres activate an ATM-ATR-dependent DNA damage response to suppress tumorigenesis," *EMBO J.*, 26:4709-4719, 2007.
International Preliminary Report on Patentability issued in corresponding PCT Application PCT/US16/019692, dated Sep. 8, 2017.
International Search Report and Written Opinion issued in corresponding PCT Application No. PCT/US16/019692, dated Jul. 26, 2016.
Kiefer et al., "Sall1-dependent signals affect Wnt signaling and ureter tip fate to initiate kidney development," *Development*, 137:3099-3106, 2010.
Lauberth et al., "A Conserved 12-Amino Acid Motif in Sall1 Recruits the Nucleosome Remodeling and Deacetylase Corepressor Complex," *J. Biol. Chem.*, 281(33):23922-23931, 2006.
Lauberth et al., "A Phosphomimetic Mutation in the Sall1 Repression Motif Disrupts Recruitment of the Nucleosome Remodeling and Deacetylase Complex and Repression of Gbx2," *J. Biol. Chem.*, 282(48):34858-34868, 2007.
Lu et al., "Stem Cell Factor SALL4 Represses the Transcriptions of PTEN and SALL1 through an Epigenetic Repressor Complex," *PLoS One* 4(5):e5577, 2009.
Osafune et al., "Identification of multipotent progenitors in the embryonic mouse kidney by a novel colony-forming assay," *Development*, 133(1):151-161, 2006.
Rodier et al., "Persistent DNA damage signaling triggers senescenceassociated inflammatory cytokine secretion," *Nat. Cell Biol.*,11(8):973-979, 2009.
Wolf et al., "An in vivo RNAi screen identifies SALL1 as a tumor suppressor in human breast cancer with a role in CDH1 regulation," *Oncogene*, 33(33):4273-7278, 2014.
Yang et al., "Genome-wide analysis reveals Sall4 to be a major regulator of pluripotency in murine-embryonic stem cells," *Proc. Natl. Acad. Sci. U.S.A.*, 105(50):19756-19761, 2008.
Yang et al., "SALL4 is a key regulator of survival and apoptosis in human leukemic cells,"*Blood*, 112:805-813, 2008.

* cited by examiner

*Primary Examiner* — Robert M Kelly
(74) *Attorney, Agent, or Firm* — Parker Highlander PLLC

(57) ABSTRACT

The present disclosure relates to the SALL1 tumor suppressor. Methods of employing SALL1 to treat cancer, as well as the underlying mechanism by which this occurs, also are described.

19 Claims, 22 Drawing Sheets

Specification includes a Sequence Listing.

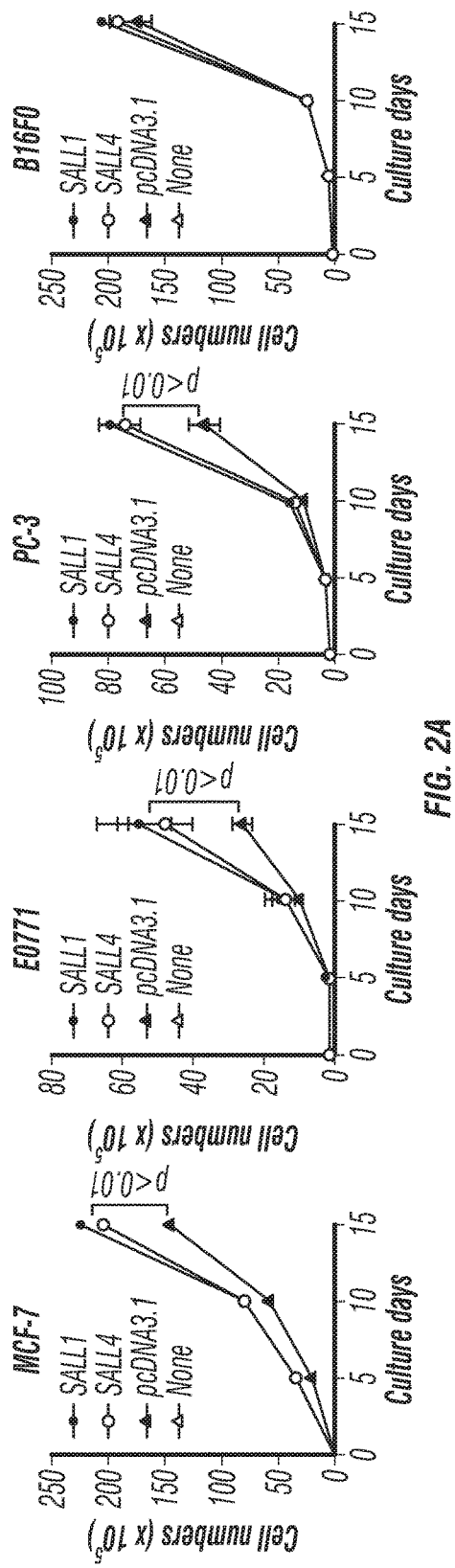
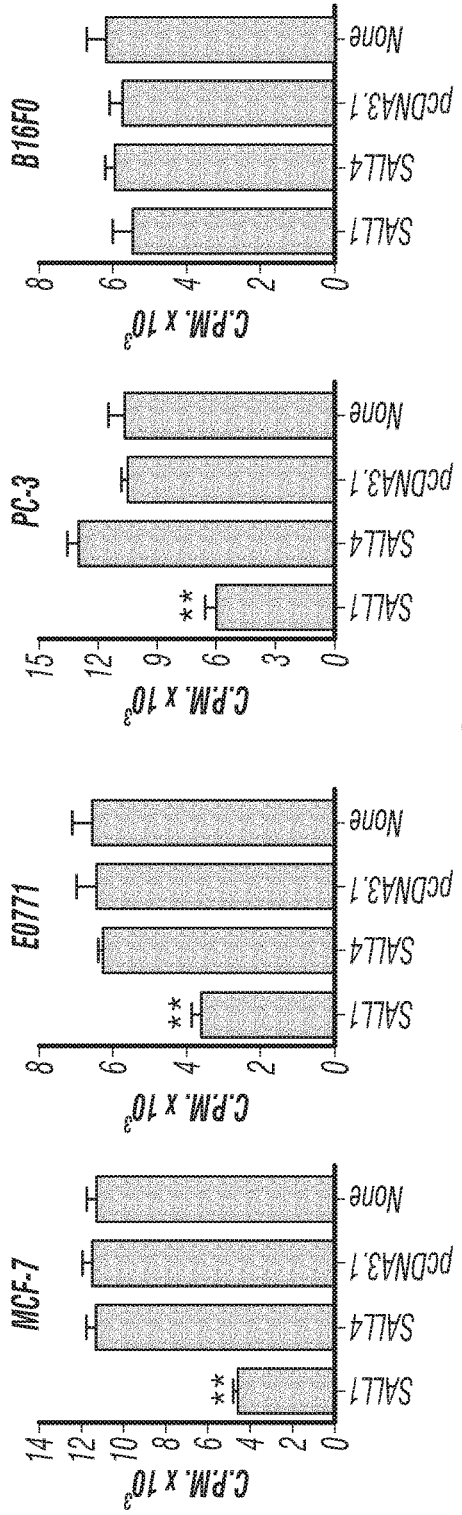
FIG. 2A
FIG. 2B

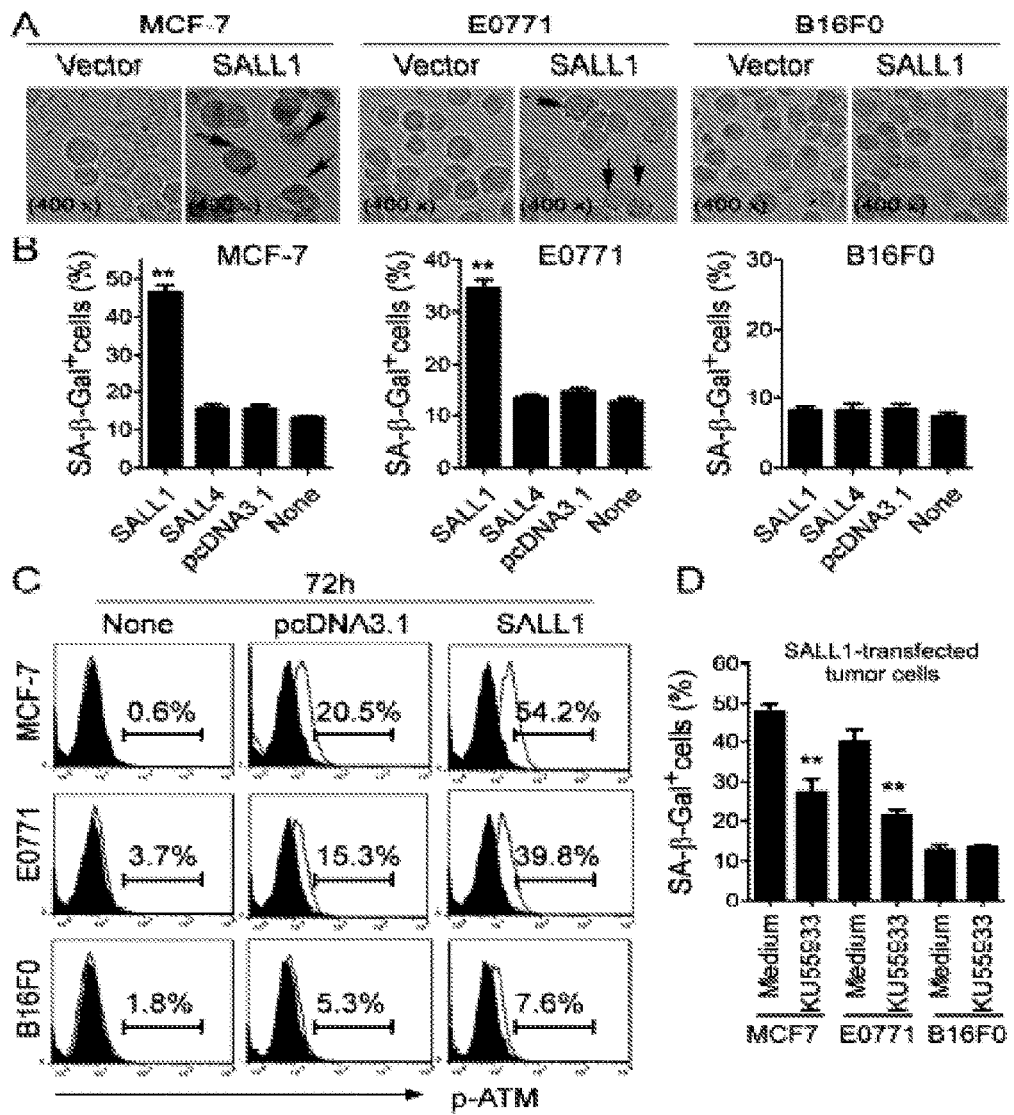
FIGS. 3A-D

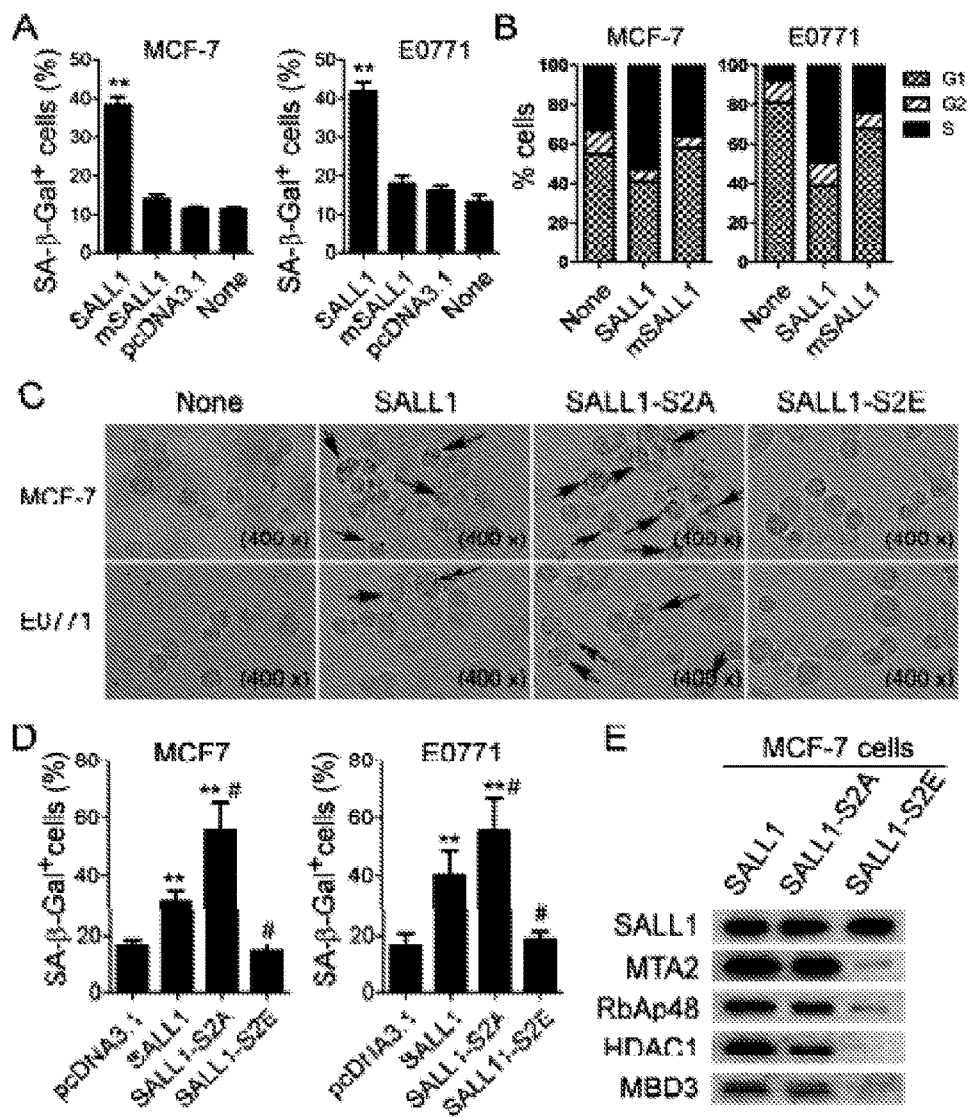
FIGS. 4A-E

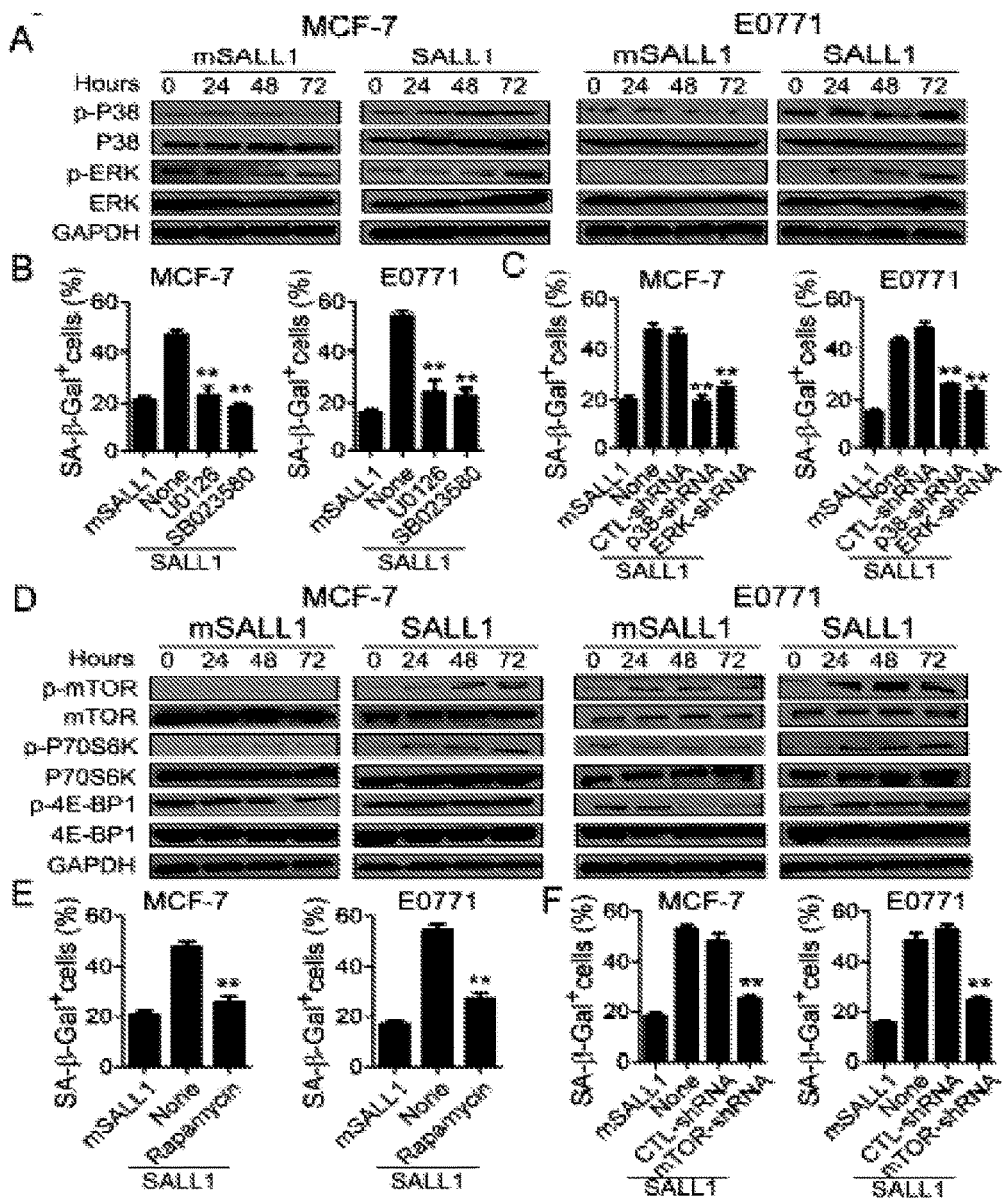
FIGS. 5A-F

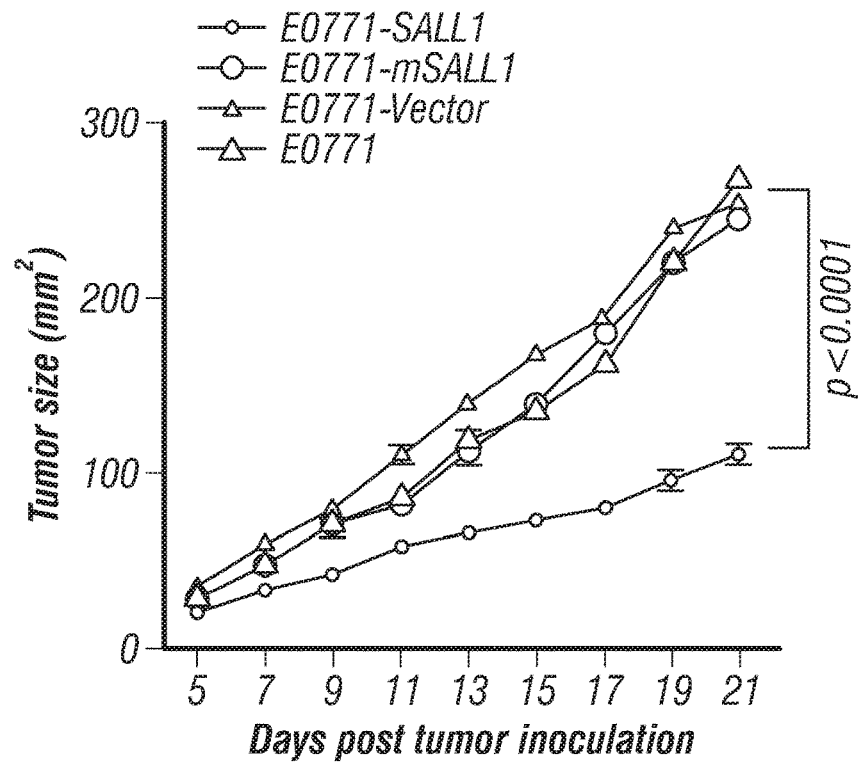
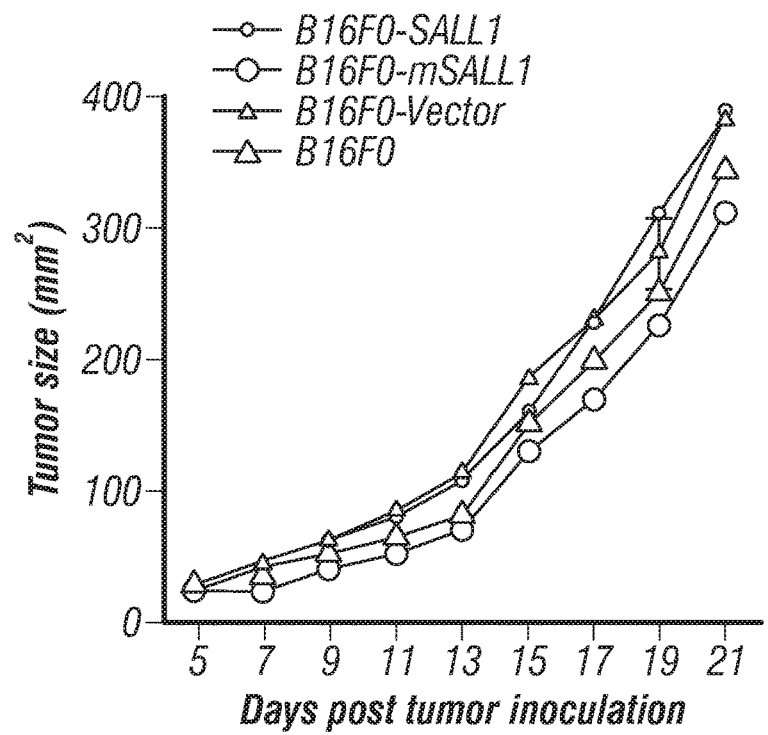
FIG. 6A

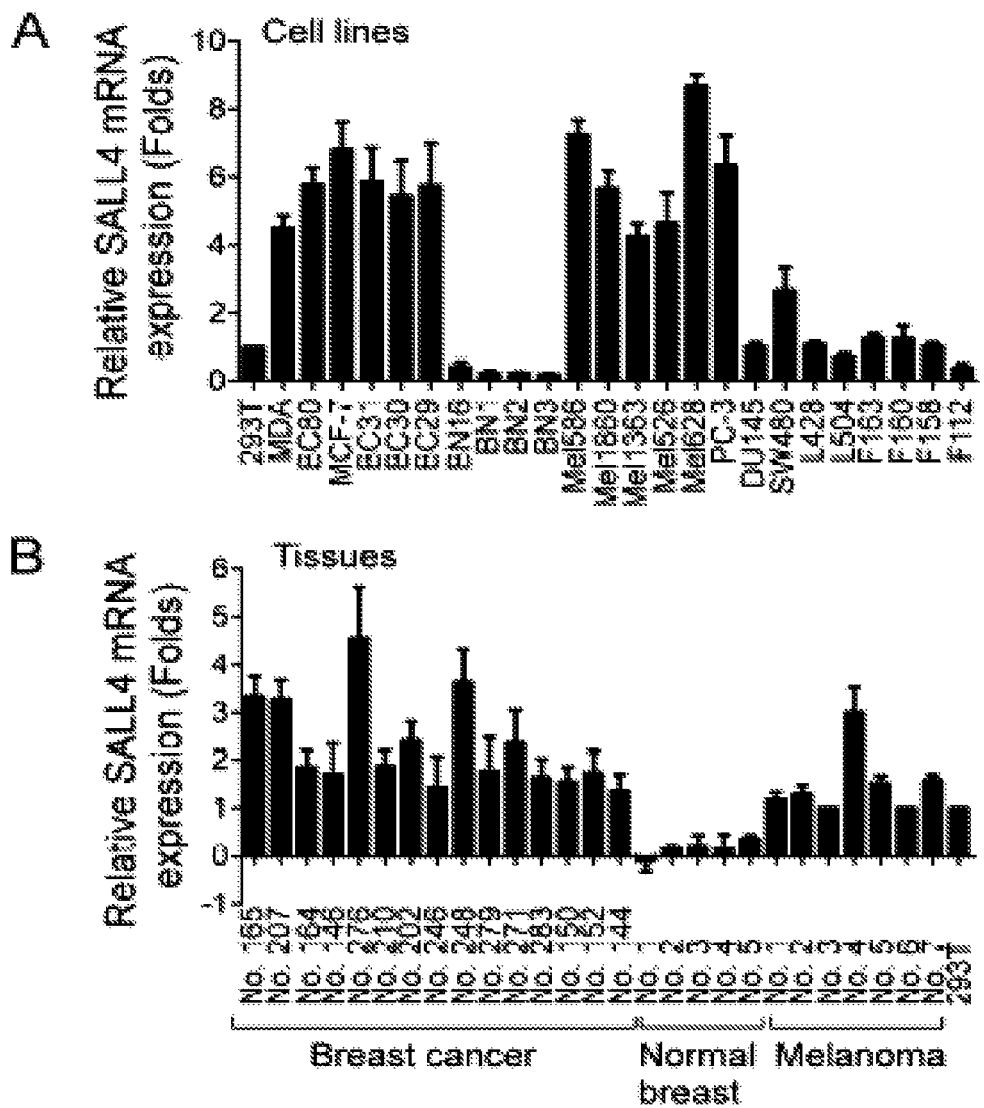
FIGS. 8A-B

FIGS. 10A-B

TUMOR SUPPRESSOR SALL1 AS A THERAPEUTIC AGENT FOR TREATING CANCER

This application is a national phase application under 35 U.S.C. § 371 of International Application No. PCT/US2016/019692, filed Feb. 26, 2016, which claims benefit of priority to U.S. Provisional Application 62/126,105, filed Feb. 27, 2015, the entire contents of each of which are hereby incorporated by reference.

BACKGROUND

I. Field

The present disclosure relates to the fields of oncology, genetics and molecular biology. More particular the disclosure relates to the use of SALL1 as a tumor suppressive cancer therapy.

II. Related Art

The human SALL gene family, SALL1-SALL4, was identified as homologues to the *Drosophila* homeotic gene spalt (Al-Baradie et al., 2002; Kohlhase et al., 1999 and Kohlhase et al., 1996). The originally identified functions of SALL family are zinc finger transcription factors as critical regulators for development of multiple organs, including kidney, heart, and normal hematopoietic system (Kiefer et al., 2010; Kiefer et al., 2008; Sato et al., 2004 and Denner and Rauchman, 2013). Mutations in the human SALL1 and SALL4 genes result in Townes-Brocks (TBS) and Okihiro syndrome (OS), respectively (Al-Baradie et al., 2002; Kiefer et al., 2008 and Borozdin et al., 2004). The SALL gene family is also important for the control of stem cell pluripotency, differentiation and self-renewal properties involving transcriptional and epigenetic actions (Denner and Rauchman, 2013; Yang et al., 2008; Osafune et al., 2006 and Lu et al., 2009).

Besides the regulation of organ and stem cell development, the role of SALL genes in tumor biology and tumorigenesis has been recently investigated. SALL2 has been reported as a potential tumor suppressor in ovarian cancer and wilms tumor (Ma et al., 2001; Li, et al., 2001 and Li, et al., 2004). SALL4 was shown to regulate survival and apoptosis in human leukemic cells (Yang et al., 2008 and Li et al., 2013). Furthermore, SALL4 was recently identified as a novel marker for hepatoblastoma, non-small cell lung carcinoma, metastatic yolk sac tumor and gastric cancinoma (Gnemmi et al., 2013; Cao et al., 2009 and Ushiku et al., 2010). Mutations in SALL3 have been discovered in a significant proportion of Burkitt's lymphoma cases (Love et al., 2012). It has been shown that SALL1 was methylated in breast and other epithelial cancers (Hill et al., 2010), but little is known about the role of SALL1 in the pathogenesis of human cancers. A recent report identified SALL1 as a tumor suppressor in human breast cancer, using an in vivo RNAi screen strategy (Wolf et al., 2014). However, the molecular mechanism and causative role of SALL1 in the regulation of breast cancer development and tumorigenesis are not well understood.

Role of SALL1 in the regulation of orgenogenesis including kidney development has been extensively studied by the inventors' group and others. In an effort to identify the molecular mechinasms responsible for SALL1 gene in kindey development regulation, the inventors have demonstrated that endogenous SALL1 recruits and binds to the nucleosome remodeling and deacetylase corepressor complex (NuRD) performing its transcriptional repression and regulation of specific developmental processes (Kiefer et al., 2010; Denner and Rauchman, 2013; Lauberth et al., 2007 and Lauberth & Rauchman, 2006). The inventors further identified a highly conserved 12-amino acid motif in the SALL1 that is sufficient for the recruitment of NuRD (Lauberth & Rauchman, 2006). In addition, they showed that protein kinase C phosphorylates serine 2 of SALL1 repression motif is the determinant for SALL1-mediated NuRD recruitment and functions (Lauberth et al., 2007). They also demonstrated that SALL1 and NuRD regulation in TBS and kidney development involves Wnt signaling (Kiefer et al., 2010 and Sato et al., 2004). Importantly, increasing evidence suggest that NuRD protein complex plays essential role in cancer development and metastasis program (Lai & Wade, 2011). Specifically, several subunits of NuRD, such as MTA1, MTA3, and Mi-2 can directly control the cancer invasive growth, epithelial-to-mesenchymal transition, and metastasis in breast cancer (Lai & Wade, 2011; Wang et al., 2009; Fujita et al., 2003 and Fu et al., 2011). Given the recent study identifying that SALL1 could be as a tumor suppressor in human breast cancer (Wolf et al., 2014), it is urgent to determine how SALL1 regulates breast cancer cell biology and functions. In addition, whether SALL1 also utilizes the similar mechanism recruiting NuRD complex and performing its suppressor function in breast cancer is unclear. Improved understanding of these molecular processes mediated by SALL1 for the regulation of tumor biology and tumorigenesis will open new avenues to develop novel therapeutic strategies in human breast cancer and other cancers as well.

SUMMARY

Thus, in accordance with the present disclosure, there is provided an isolated polynucleotide encoding SALL1, wherein said isolated polynucleotide is operably connected to a heterologous promoter active in a mammalian cancer cell. The polynucleotide may have a nucleic acid sequence of SEQ ID NO: 1 or a complement thereof. The heterologous promoter may operable in human cancer cell, or a non-human mammal cancer cell. The promoter may be selected from the group consisting of hsp68, SV40, CMV IE, MKC, $GAL4_{UAS}$, HSV and β-actin. The promoter may be a tissue specific promoter or an inducible promoter. The promoter may be active in a human breast cancer cell or a human melanoma cell. The polynucleotide may be contained in a replicable expression vector, such as a viral vector, for example selected from the group consisting of a retroviral vector, an adenoviral vector, and adeno-associated viral vector, a vaccinia viral vector, and a herpesviral vector.

Also provided is a method for suppressing the growth, proliferation, migration or metastasis of a cancer cell comprising contacting said cells with an expression cassette comprising a polynucleotide encoding SALL1, wherein said polynucleotide is under the control of a promoter operable in eukaryotic cells. The polynucleotide may have a nucleic acid sequence of SEQ ID NO: 1 or a complement thereof. The promoter may be heterologous to the polynucleotide sequences. The heterologous promoter may operable in a human cancer cell, or a non-human mammal cancer cell. The promoter may be selected from the group consisting of hsp68, SV40, CMV IE, MKC, $GAL4_{UAS}$, HSV and β-actin. The promoter may be a tissue specific promoter or an inducible promoter. The promoter may be active in a human breast cancer cell or a human melanoma cell. The expression cassette may further comprise a polyadenylation signal. The polynucleotide may be contained in a replicable expression vector, such as a viral vector, for example selected from the group consisting of a retroviral vector, an adenoviral vector, and adeno-associated viral vector, a vaccinia viral vector, and a herpesviral vector. The replicable expression vector is a non-viral vector, such as one encapsulated in a lipid delivery vehicle or a nanoparticle.

The method may further comprise contacting said cancer cell with a second anti-cancer therapy, such as radiation therapy, gene therapy, hormonal therapy, immunotherapy, toxin therapy or surgery. The cancer cell may be derived from a tissue selected from the group consisting of brain, lung, liver, spleen, kidney, lymph node, small intestine, blood, pancreas, colon, stomach, breast, endometrium, prostate, testicle, ovary, skin, head and neck, esophagus, bone marrow and blood tissue. The cancer cell may be located in a human subject, and the expression cassette may be administered systemically, administered local or regional to a tumor site, administered by intra-tumoral injection or to a resected tumor bed, and/or administered more than once. The method may further comprising assessing SALL1 structure, expression and/or function in a sample from said subject.

In still another embodiment, there is provided a method for suppressing the growth, proliferation, migration or metastasis of a cancer cell comprising the step of contacting a cancer cell with SALL1 polypeptide. The SALL1 polypeptide may be encapsulated in a lipid delivery vehicle or a nanoparticle. The cancer cell may be derived from a tissue selected from the group consisting of brain, lung, liver, spleen, kidney, lymph node, small intestine, blood, pancreas, colon, stomach, breast, endometrium, prostate, testicle, ovary, skin, head and neck, esophagus, bone marrow and blood tissue. The cancer cell may be located in a human subject, and the SALL1 polypeptide may be administered systemically, administered local or regional to a tumor site, administered by intra-tumoral injection or to a resected tumor bed, and/or administered more than once. The method may further comprising assessing SALL1 structure, expression and/or function in a sample from said subject. The method may further comprise contacting said cancer cell with a second anti-cancer therapy, such as radiation therapy, gene therapy, hormonal therapy, immunotherapy, toxin therapy or surgery.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein:

(FIGS. 1A-B) Gene expression levels of SALL1 in different cancer cell lines (FIG. 1A) and in tumor tissues (FIG. 1B) using Real-time PCR analyses. Tumor cell lines include breast cancer (human MDA, MCF7, BC80, 31, 30, 29, 16, 12 and 10), melanoma (Mel1938, Mel1586, Mel1860, Mel1363, Mel1526 and Mel1628), prostate cancer (PC3 and DU145), colon cancer (SW480), and lymphoma (L428 and L504). Normal breast cell lines (BN6 and BN16) and fibroblasts (F163, F160, F158 and F112) and 293T cells were included as controls. mRNA levels in each cell line and tissue were normalized to the relative quantity of GAPDH expression and then adjusted to SALL1 levels in 293 T cells (set as 1). Results shown in the histogram are mean±SD from three independent experiments. (FIGS. 1C-D) Association analyses of SALL1 expression with specific breast cancer subtypes. The data sets were accessed from the TCGA breast cancer Argilent microarray expression database downloaded from the cBioPortal (world-wide-webe at cbioportal.org). The box plot indicated the log 2 transformed mRNA median expression level of SALL1 in the tissues. N indicated the number of sample size of each tissue type. Mann-Whitney analysis was used to compare the SALL1 expression across the different breast cancer subtypes and normal tissues, and **$p<0.01$ within the comparison groups. (FIGS. 1E-F) SALL1 expression in tumor cells in breast cancer and melanoma tissues were determined using the immunohistochemical staining. Significantly increased numbers of SALL1$^+$ tumor cells in melanoma tissues were much higher than those in breast cancer tissues. Expression level of each dot shown in FIG. 1F is the average numbers of SALL1$^+$ cells per high field (400×) in each tissue sample. The median number of SALL1$^+$ cells in each group is shown as a horizontal line. Significance was determined by unpaired T test. (FIGS. 1G-H) SALL1 expression levels in breast cancer tissues with different ER and HER2 statuses. SALL1$^+$ cell population in ER$^+$ patients was significantly higher than that in ER$^-$ patients. Furthermore, SALL1$^+$ cell numbers in HER2$^+$ patients were much higher than that in HER2$^-$ patients. Tissue immunohistochemical staining and cell number counting were identical as in FIG. 1E. Significance was determined by unpaired T test.

(FIG. 2A-B) Transfection of SALL1 but not SALL4 significantly inhibited breast cancer and prostate cancer cell growth and proliferation. However, over-expression of SALL1 in B16F0 melanoma cells (control) did not affect cell growth and proliferation. Tumor cells transfected with or without plasmids pcDNA3.1-SALL1, pcDNA3.1-SALL4, and pcDNA3.1, were cultured at a started number of $2\times10^4$/well in 24 wells (FIG. 2A), or $5\times10^4$/well in 96-well plates (FIG. 2B). Cell growth was evaluated at different time points using cell number counting (FIG. 2A), and cell proliferation was determined using [$^3$H]-thymidine assays (FIG. 2B). Data are mean±SD from three independent experiments with similar results. **$p<0.01$ compared with the vector control group. (FIG. 2C) The suppression of breast cancer cell proliferation and growth mediated by SALL1 expression is not due to cell apoptosis. Transfected breast cancer and melanoma cells were cultured for additional 72 hours. Apoptosis in transfected tumor cells was analyzed after staining with PE-labeled Annexin V and 7-AAD. Data shown are representative of three independent experiments with similar results. (FIG. 2D) SALL1 transfection in both MCF-7 and E0771 cells, but not in melanoma B16F0 cells significantly promoted cancer cell arrest in S phase and decrease in G0/G1 phase. Cell treatment was the same as in FIG. 2C. Cell cycle distribution in tumor cells was analyzed after incubation with 10 µg/ml propidium iodide and 100 µg/ml RNase A. B16F0 melanoma cells served as a control. Data are representative of three independent experiments with similar results.

FIGS. 3A-D. SALL1 over-expression in breast cancer cells induces tumor cell senescence and ATM-associated DNA damage response. (FIGS. 3A-B) Transfection of SALL1, but not SALL4 in MCF-7 and E0771 cancer cells significantly induced the increased SA-β-Gal$^+$ cell populations. In contrast, over-expression of SALL1 in B16F0 cells did not increase senescent cell populations. Transfected tumor cells were cultured for additional 5 days. Senescent cells were analyzed using the SA-β-Gal activity assay and the SA-β-Gal$^+$ tumor cells were identified with dark blue granules as indicated by the arrows (FIG. 3A). Data shown in FIG. 3B are mean±SD from three independent experiments with similar results. $p<0.01$ compared with the vector control group. (FIG. 3C) SALL1 expression in breast cancer cells induced phosphorylated activation of ATM in the transfected cells. Transfected tumor cells were determined for the p-ATM expression after culture for 3 additional days using FACS analyses. (FIG. 3D) Pretreatment of breast cancer cells with an ATM specific inhibitor KU55933 significantly prevented the induction of tumor cell senescence induced by SALL1 expression. Tumor cells were pretreated with or without KU55933 (20 µM) for 1 day, and then transfected with SALL1. SA-β-Gal expression in the transfected tumor cells was determined with SA-β-Gal staining after culture for 3 additional days. Data shown are mean±SD from three independent experiments, and paired t-test was performed. $p<0.01$, compared with the medium only group.

FIGS. 4A-E. Involvement of NuRD complex in the regulation of breast cancer cell senescence and suppression mediated by SALL1. (FIGS. 4A-B) Transfection of mutated SALL1 (deleted the NuRD binding peptide motif of conserved 12-amino) in MCF-7 and E0771 cancer cells did not induce SA-β-Gal$^+$ cell populations (FIG. 4A) and promote cancer cell cycle arrest in S phase (FIG. 4B). In contrast, transfection of full-length SALL1 into MCF-7 and E0771 breast cancer cells significantly induced tumor cell senescence (around 40%) and promoted cell cycle arrest in S phase. Breast cancer cells were transfected with the indicated constructs and cultured for additional 72 hours. Senescent cells were analyzed using the SA-β-Gal activity assay and the cell cycle distribution in tumor cells was analyzed after incubation with propidium iodide. Data shown in FIG. 4A are mean±SD from three independent experiments with similar results. $p<0.01$ compared with the mSALL1 and vector control groups. (FIGS. 4C-D) Transfection of SALL1-S2E into MCF-7 and E0771 breast cancer cells lost the ability to induce tumor cell senescence. However, transfection of SALL1-S2A into breast cancer cells significantly augmented senescence induction in both cell lines compared with that of in wild-type SALL1-transfected tumor cells. Cell transfection procedure and SA-β-Gal$^+$ cell determination were identical to (A). SALL1-S2E: substitution of the serine with a glutamic acid in SALL1. SALL1-S2A: mutating the serine to an alanine in SALL1. SA-β-Gal$^+$ tumor cells were identified with dark blue granules as indicated by the arrows (in C). Data shown in (FIG. 4D) are mean±SD from three independent experiments with similar results. $p<0.01$, compared with the vector control group. #$p<0.01$, compared with the wild-type SALL1 group. (FIG. 4E) Transfection of wild-type SALL1 and SALL1-S2A into MCF-7 tumor cells significantly recruited NuRD complex components determined with the immunoprecipitation analyses. In contrast, transfection of SALL1-S2E markedly disrupted NuRD recruitment and its component expression. MCF-7 cells were transfected with or without plasmids pEBG-SALL1, pEBG-SALL1-S2A, and pEBG-SALL1-S2E, and cultured for 3 days. Total protein lysates were mixed with monoclonal antibody against an N-terminal epitope of SALL1 and then precipitated with Protein G-Sepharose beads. Immunoprecipitates were analyzed by western blotting with antibodies against SALL1, HDAC1, MTA2, MBD3 and RbAp46/48.

FIGS. 5A-F. MAPK p38 and ERK1/2, and mTOR signaling pathways control the molecular process of SALL1-induced breast cancer cell senescence. (FIG. 5A) Transfection of wild-type SALL1 but not mutated SALL1 in MCF-7 and E0771 cells induced phosphorylation of ERK and p38 in senescent tumor cells. Transfected breast cancer cells were cultured for different time points and cell lysates were prepared for western blot analyses. (FIG. 5B) Inhibition of ERK1/2 or p38 signaling pathways by specific pharmacological inhibitors significantly prevented breast cancer cell senescence induced by SALL1 expression, resulting in decreased SA-β-Gal expression. SALL1-transfected MCF-7 and E0771 cancer cells were co-cultured in the presence or absence of inhibitors U0126 or SB203580 (10 µM) for 5 days. The treated tumor cells were analyzed with SA-β-Gal expression. Data shown are mean±SD from three independent experiments with similar results. $p<0.01$, compared with the SALL1-transfected group but not treated with inhibitor. (FIG. 5C) Knockdown of ERK1/2 and p38 genes by shRNA in MCF-7 and E0771 cells dramatically blocked SALL1-induced tumor cell senescence. Breast cancer cells were transfected with lenti-shRNAs specific for ERK1/2 or p38 molecules. Transduced (GFP$^+$) cancer cells were purified by FACS sorting and then transfected with SALL1 and cultured for 5 days. The SA-β-Gal$^+$ cancer cells were determined. $p<0.01$, compared with the group transduced with control shRNA. Data shown are representative of three independent experiments with similar results. (FIG. 5D) Phosphorylation and subsequent activation of mTOR signaling in breast cancer cells transfected with SALL1 but not mSALL1. Transfected MCF-7 and E0771 cells cultured for different times, and then were collected for western blot analyses of total and phosphorylated mTOR, p70S6K, and 4E-BP1 protein levels. (FIG. 5E) Rapamycin markedly inhibited the SALL1-mediated breast cancer cell senescence. SALL1-transfected MCF-7 and E0771 cancer cells were co-cultured in the presence or absence of mTOR inhibitor rapamycin (5 µM) for 5 days. The treated tumor cells were stained for SA-β-Gal expression. Data shown are mean±SD from three independent experiments with similar results. $p<0.01$, compared with the SALL1-transfected group but not treated with inhibitor. (FIG. 5F) Knockdown of mTOR by shRNA in MCF-7 and E0771 cells significantly blocked SALL1-induced tumor cell senescence. Transfection procedure was identical to FIG. 5C and SA-β-Gal$^+$ cancer cells were determined. $p<0.01$, compared with the group transduced with control shRNA. Data shown are representative of three independent experiments with similar results.

FIGS. 6A-D. SALL1 over-expression in breast cancer cells inhibited tumor growth and development in vivo. (FIG. 6A) Over-expression of SALL1 in E0771breast cancer cells dramatically inhibited tumor growth in NSG immunodeficient mice. However, SALL1 over-expression in B16F0 melanoma cells did not affect tumor development. E0771 ($2\times10^5$/mouse) and B16F0 ($1\times10^5$/mouse) tumor cells infected with lentivirus carrying SALL-1, mSALL-1 or vector, were subcutaneously injected into NSG mice. Tumor volumes were measured and presented as mean±SD (n=5 mice per group). P values were determined by the one-way analysis of variance (ANOVA). Similar results were obtained in three repeated experiments. (FIG. 6B) Representative image of the xenograft tumors obtained from the indicated groups at the endpoint of the experiments (day 21). (FIG. 6C) E0771 breast cancer cells over-expressed SALL1 had much lower tumor weight compared with that of other groups. Furthermore, SALL1 over-expression in B16F0 melanoma cells did not affect tumor weight. Results shown are mean±SD of the xenograft tumor weights from the indicated groups in the two models at the endpoint of the experiments (day 21) (n=5 mice per group). $p<0.01$, compared with the control groups transfected with mSALL1 and vector using unpaired t-test. (FIG. 6D) Large amounts of senescent tumor cells were observed in SALL1-transfected E0771 tumor tissues in NSG mice. SA-β-Gal expression was determined in the tumor frozen tissues from different groups at the endpoint of experiment. Left panels are photomicrographs of SA-β-Gal expression in tumor tissues from different groups. Right panel is the mean±SD of SA-β-Gal$^+$ cell numbers per high microscope field in the tumor tissues from 5 mice of each group. $p<0.01$, compared with the control mice of mSALL1 and vector groups using unpaired t-test.

(FIG. 7A) Over-expression of SALL1 in E0771 breast cancer cells significantly inhibited the migration of tumor cells compared with the control mSALL1 and vector-transfected tumor cells in the wound closure assays. Data shown are from three independent experiments with similar results. (FIG. 7B) Over-expression of SALL1 in E0771 breast cancer cells markedly suppressed the tumor cell migration and metastasis in NSG mice. Lentivirus-transfected E0771 tumor cells were stained with VivoTag®680 XL and then injected tail intravenously ($5\times10^4$/mouse) into NSG mice. Mice were imaged with the IVIS Spectrum at different time points following the tumor cell adoptive transfer into NSG mice. Data shown are the dorsal, ventral, and right lateral images of representative of 5 mice per group at 2 hours and day 5. Color bar represents signal intensity scales over whole body. (FIGS. 7C-D) Over-expression of SALL1 in E0771 cells dramatically decreased tumor macrometastatic numbers in lung and liver surfaces. Representative images shown in FIG. 7C are a representative of mouse lungs and livers obtained from the indicated groups at the endpoint of the experiments. Tumor metastatic spots were counted and results shown are mean±SD in FIG. 7D (n=5 mice per group). **$p<0.01$, compared with the control groups transfected with mSALL1 and vector using unpaired t-test. (FIG. 7E) H & E staining on sections from embedded lung tissues showed that high amount of tumor cells infiltrated into lungs obtained from control groups (mSALL1 and vector), but not from the SALL1 transfection group.

FIGS. 8A-B. SALL4 expression levels in different types of human cancers. (FIGS. 8A-B) Gene expression levels of SALL4 in different cancer cell lines (FIG. 8A) and in tumor tissues (FIG. 8B) using Real-time PCR analyses. Tumor cell lines include breast cancer (human MDA, MCF7, BC80, 31, 30, 29, 16, and murine 4T1 and E0771), melanoma (Mel1938, Mel1586, Mel1860, Mel1363, Mel1526 and Mel1628, and murine B16F0), prostate cancer (PC3 and DU145), colon cancer (SW480), and lymphoma (L428 and L504). Normal breast cell lines (BN6 and BN16) and fibroblasts (F163, F160, F158 and F112), 293T cells, and normal breast tissues were included as controls. mRNA levels in each cancer cell line and tumor tissue were normalized to the relative quantity of GAPDH expression and then adjusted to the express levels in 293T cells (set as 1). Results shown in the histogram are mean±SD from three independent experiments.

(FIG. 10A) Transfection of SALL1, but not SALL4 in MCF-7 and E0771 cancer cells significantly induced the increased SA-β-Gal$^+$ cell populations. In contrast, over-expression of SALL1 in B16F0 cells did not induce senescent cells. Transfected tumor cells were cultured for additional 3 days, and senescent cells were analyzed using the SA-β-Gal activity assay. Data shown are mean±SD from three independent experiments with similar results. **$p<0.01$ compared with the vector group. (FIG. 10B) SALL1 expression in breast cancer cells induced phosphorylated activation of ATM in the transfected cells. Transfected tumor cells were determined for the p-ATM expression after culture for 24 hours using the FACS analysis.

(FIG. 13A) Over-expression of SALL1 in MCF-7 breast cancer cells significantly inhibited the migration of tumor cells compared with the control mSALL1 and vector-transfected tumor cells in the wound closure assays. Data shown are from three independent experiments with similar results. (FIG. 13B) Over-expression of SALL1 in E0771 breast cancer cells markedly suppressed the tumor cell migration and metastasis in NSG mice. Lentivirus-transfected E0771 tumor cells were stained with VivoTag® 680 XL and then injected tail intravenously (5×10⁴/mouse) into NSG mice. Mice were imaged with the IVIS Spectrum at different time points following the tumor cell adoptive transfer. Data shown are the dorsal, ventral, and right lateral images of representative of 5 mice per group at day 3 and day 10. (FIG. 13C) H & E staining on sections from embedded liver tissues showed that high amount of tumor cells infiltrated into livers obtained from control groups (mSALL1 and vector), but not from the SALL1 transfection group.

DETAILED DESCRIPTION OF THE EMBODIMENTS

Figure 1A:
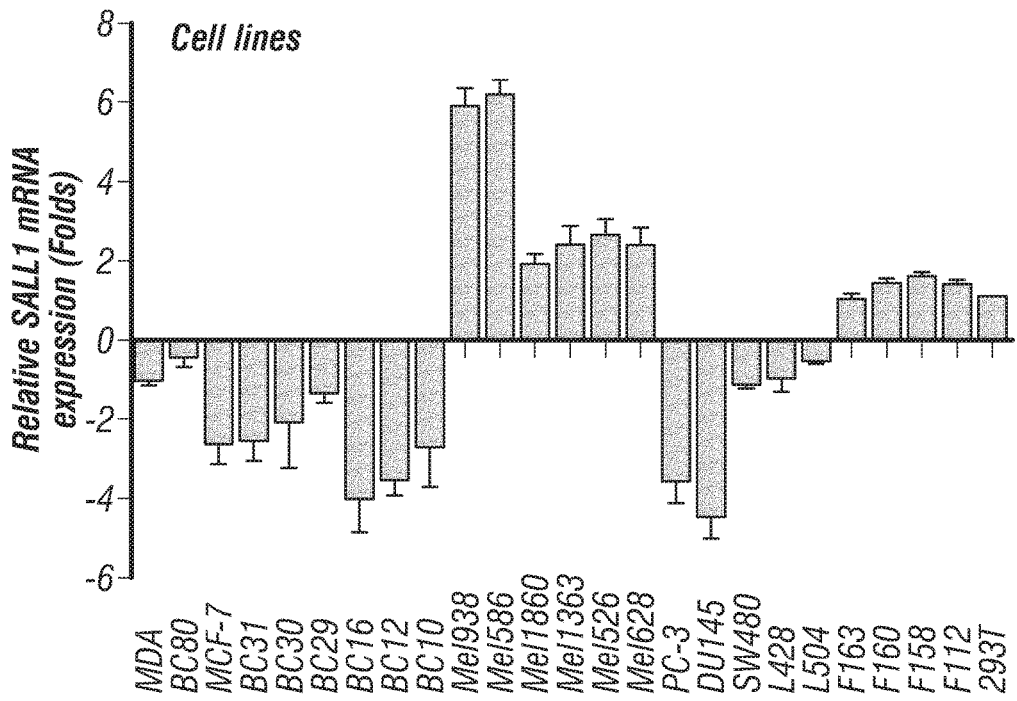
FIGS. 1A-H. SALL1 expression is down-regulated in human breast cancer.

To better understand the role of SALL1 in the pathogenesis of breast cancer, the inventors investigated the mechanism of SALL1 tumor suppressor activity in breast cancer models. Using a gain-of function strategy, they showed that SALL1 expression in breast cancer cells inhibited tumor cell growth and proliferation, promoted cell cycle arrest, and induced cell senescence. They further revealed that SALL1 tumor suppressor activity depended on its ability to recruit NuRD and that this molecular process was controlled by MAPK p38 and ERK1/2, and mTOR signaling pathways in cancer cells. In addition, complementary in vivo studies further demonstrated that SALL1 expression and NuRD recruitment in breast tumor cells inhibited tumorigenesis and metastasis in breast cancer models. These studies collectively show that SALL1 functions as a tumor suppressor in breast cancer that directly controls cancer cell fate and metastasis and can provide tumor suppressing activity when provided exogenously. These and other aspects of the disclosure are discussed below.

I. SALL1

According to the present disclosure, SALL1 will be utilized as a tumor suppressor. This molecule is capable of suppressing tumor phenotypes and oncogenic functions in various cancers. In addition to the entire SALL1 molecule, the present disclosure also relates to fragments of the polypeptide that may retain the tumor suppressing activity, including synthetic peptides. SALL1 and fragments thereof may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Features of the Polypeptide

Sal-like 1 (Drosophila), also known as SALL1, is a protein which in humans is encoded by the SALL1 gene. As the full name suggests, it is one of the human versions of the spalt (sal) gene known in Drosophila. The protein encoded by this gene is a zinc finger transcriptional regulator and may be part of the NuRD histone deacetylase (HDAC) complex. Defects in this gene are a cause of Townes-Brocks syndrome (TBS) as well as branchio-oto-renal syndrome (BOR). At least two transcript variants encoding different isoforms have been found for this gene.

B. Variants of SALL1

Amino acid sequence of SALL1 is described in SEQ ID NO: 1. Variants of this sequence may be substitutional, insertional or deletion variants. Deletion variants lack one or more residues of the native protein which are not essential for function or immunogenic activity. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent or improved molecule. For example, certain amino acids may be substituted for other amino acids in a protein structure without appreciable loss of interactive binding capacity with structures such as. Certain amino acid substitutions can be made in a protein sequence, or to the underlying DNA coding sequence, and nevertheless obtain a protein with like properties. It is thus contemplated by the inventors that various changes may be made in the DNA sequences of genes without appreciable loss of their biological utility or activity, as discussed below. In fact, in certain cases, substitutions may improve activity, such as an S→A substitution at residue 2. Table 1 shows the codons that encode particular amino acids.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids provide hydropathic indices are within ±2, are within ±1, and within ±0.5.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids provides hydrophilicity values within ±2, within ±1, and within ±0.

As outlined above, amino acid substitutions are generally based on the relative similarity of the amino acid side-chain substituents, for example, their hydrophobicity, hydrophilicity, charge, size, and the like. Exemplary substitutions that take certain of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the disclosure is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of SALL1, but with altered and even improved characteristics.

C. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It will be desirable to purify SALL1 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A particular method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fructose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

III. Nucleic Acids

The present disclosure also provides, in another embodiment, genes encoding SALL1. A gene for the human SALL1 molecule has been identified. The present disclosure is not limited in scope to this gene, however, as one of ordinary skill in the art could readily identify related homologs in various other species (e.g., mouse, rat, rabbit, dog, monkey, gibbon, chimp, ape, baboon, cow, pig, horse, sheep, cat and other species).

In addition, it should be clear that the present disclosure is not limited to the specific nucleic acids disclosed herein. As discussed below, a "SALL1 gene" may contain a variety of different bases and yet still produce a corresponding polypeptide that is functionally indistinguishable from, and in some cases structurally identical to, the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present disclosure may prove useful in the context of screening for agents that induce, repress, inhibit, augment, interfere with, block, abrogate, stimulate or enhance the function of SALL1.

A. Nucleic Acids Encoding SALL1

Nucleic acids according to the present disclosure may encode an entire SALL1 protein, as shown in SEQ ID NO: 2, a domain of SALL1 that expresses a tumor suppressing function, or any other fragment of the SALL1 sequences set forth herein. The nucleic acid may be derived from genomic DNA, i.e., cloned directly from the genome of a particular organism. In particular embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present disclosure may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is desired, such as where the non-coding regions are required for optimal expression or where non-coding regions such as introns are to be targeted in an antisense strategy.

It also is contemplated that a given SALL1 from a given species may be represented by natural variants that have slightly different nucleic acid sequences but, nonetheless, encode the same protein (see Table 1, above).

As used in this application, the term "a nucleic acid encoding a SALL1" refers to a nucleic acid molecule that has been isolated free of total cellular nucleic acid. In certain embodiments, the disclosure concerns a nucleic acid sequence essentially as set forth in SEQ ID NO: 2. The term "as set forth in SEQ ID NO: 2" means that the nucleic acid sequence substantially corresponds to a portion of SEQ ID NO: 2. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 70%, most usually about 80%, at least about 90% and at least about 95%, and at least about 98% or 99% of nucleotides that are identical to the nucleotides of SEQ ID NO: 2. Sequences that are essentially the same as those set forth in SEQ ID NO: 2 also may be functionally defined as sequences that are capable of hybridizing to a nucleic acid segment containing the complement of SEQ ID NO: 2 under standard conditions.

The DNA segments of the present disclosure include those encoding biologically functional equivalent SALL1 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present disclosure also encompasses DNA segments that are complementary, or essentially complementary, to the sequence set forth in SEQ ID NO: 2. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 under relatively stringent conditions such as those described herein. Such sequences may encode the entire SALL1 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present disclosure is in the search for genes related to SALL1 or, more particularly, homologs of SALL1 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present disclosure is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is used, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Vectors for Cloning, Gene Transfer and Expression

Within certain embodiments, expression vectors are employed to express the SALL1 polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control" and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific (including for particular type sof cancer cells), inducible, and/or useful under the appropriate conditions to direct high level expression of the introduced DNA segment. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present disclosure. Some such promoters are set forth in Tables 2 and 3.

TABLE 2

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas | Type II pneumocytes; Clara cells |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |

TABLE 2-continued

Candidate Tissue-Specific Promoters for Cancer Gene Therapy

| Tissue-specific promoter | Cancers in which promoter is active | Normal cells in which promoter is active |
|---|---|---|
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 3

Candidate Promoters for Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell | Leukocytes |

TABLE 3-continued

Candidate Promoters for Tissue-Specific Targeting of Tumors

| Promoter | Cancers in which Promoter is active | Normal cells in which Promoter is active |
|---|---|---|
| GRP78/BiP | carcinomas of head and neck; possibly many other cancers Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

2. Splice Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference.)

3. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator may comprise a signal for the cleavage of the RNA, and the terminator signal may promote polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator, or viral termination sequences, such as for example the SV40 terminator. In certain embodiments, the termination signal may be a lack of transcribable or translatable sequence, such as due to a sequence truncation.

4. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Particular embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

7. Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670, 488). The various viral vectors described below, present specific advantages and disadvantages, depending on the particular gene-therapeutic application.

Adenoviral Vectors.

In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present disclosure comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The iv sequence is required for the packaging of the adenoviral genome.

A common approach for generating adenoviruses for use as a gene transfer vector is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present disclosure it may be convenient to introduce the transforming construct at the position from which the E1-coding sequences have been removed. However, the position of insertion of the construct within the adenovirus sequences is not critical to the disclosure. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the disclosure. The adenovirus may be of any of the 42 different known serotypes and/or subgroups A-F. Adenovirus type 5 of subgroup C is a particular starting material in order to obtain the conditional replication-defective adenovirus vector for use in the present disclosure. This is because adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Adenovirus growth and manipulation is known to those of skill in the art, and exhibits broad host range in vitro and in vivo (U.S. Pat. Nos. 5,670,488; 5,932,210; 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors.

In certain embodiments of the disclosure, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral it) proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present disclosure may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present disclosure are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present disclosure (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery include a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado et al., 1999; Engel and Kohn, 1999), cancer (Clay et al., 1999), cerebrovascular disease (Weihl et al., 1999) and hemophilia (Kay, 1998).

Herpesviral Vectors.

Herpes simplex virus (HSV) type I and type II contain a double-stranded, linear DNA genome of approximately 150 kb, encoding 70-80 genes. Wild-type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miyatake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP4? (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors.

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this disclosure, into that packaging cell yields a producer cell which releases infectious viral particles carrying the foreign gene of interest. The env is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. The heterologous sequence may be linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present disclosure, one may graft or transplant cells infected with the recombinant lentivirus ex vivo, or infect cells in vivo.

Other Viral Vectors.

The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

In certain embodiments, vaccinia viral vectors are contemplated for use in the present disclosure. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes it) to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. Nos. 5,849,304 and 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, it has a wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors.

Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

8. Non-Viral Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection:

In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present disclosure include the introduction of a nucleic acid by direct microinjection. Direct microinjection has been used to introduce nucleic acid constructs into *Xenopus* oocytes (Harland and Weintraub, 1985).

Electroporation.

In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

Calcium Phosphate.

In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading.

Additional embodiments of the present disclosure include the introduction of a nucleic acid by direct sonic loading. LTK⁻ fibroblasts have been transfected with the thymidine kinase gene by sonication loading (Fechheimer et al., 1987).

Liposome-Mediated Transfection.

In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection:

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner.

D. Expression Systems

Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAxBAc® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length C$_{MV}$ promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr that confers resistance to; gpt, that confers resistance to mycophenolic acid; neo, that confers resistance to the aminoglycoside G418; and hygro, that confers resistance to hygromycin.

III. Diagnosing Cancers with Deficiencies in SALL1

SALL1 antibodies or SALL1 nucleic acids may be employed as a diagnostic or prognostic indicator of cancer. More specifically, point mutations, deletions, insertions or regulatory pertubations relating to the reduction in expression or activity of SALL1 may cause or promote cancer development, cause or promote tumor progression at a primary site, and/or cause or promote tumore metastasis.

A. Genetic Diagnosis

One embodiment of the instant disclosure comprises a method for detecting variation in the expression of SALL1, or in the structure of the SALL1 gene or gene product. Also contemplated are epigenetic modifications, such as methylation of promoter regions. This may comprises determining that level of SALL1 or determining specific alterations in the expressed product. Such cancers with SALL1 defects may include brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue.

The biological sample can be any tissue or fluid that can contain cells. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, nipple aspirates, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have SALL1-related pathologies. In this way, it is possible to correlate the amount or structure of SALL1 detected with various clinical states.

"Alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations or epigenetic modifications in and outside the coding region also may affect the amount of SALL1 produced, both by altering the transcription of the gene or in destabilizing or otherwise altering the processing of either the transcript (mRNA) or protein.

A cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

It is contemplated that other mutations in the SALL1 gene may be identified in accordance with the present disclosure. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

B. Immunodiagnosis

Antibodies of the present disclosure can be used in characterizing the SALL1 content of healthy and diseased tissues, through techniques such as immunohistochemistry, ELISAs and Western blotting. This may provide a screen for the presence or absence of malignancy or as a predictor of future cancer.

The use of antibodies of the present disclosure, in an ELISA assay is contemplated. For example, anti-SALL1 antibodies are immobilized onto a selected surface, in particular a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface. After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for SALL1 that differs the first antibody. Appropriate conditions include diluting the sample with diluents such as BSA, bovine gamma globulin (BGG) and phosphate buffered saline (PBS)/Tween®. These added agents also tend to assist in the reduction of nonspecific background. The layered antiserum is then allowed to incubate for from about 2 to about 4 hr, at temperatures on the order of about 25° to about 27° C. Following incubation, the antisera-contacted surface is washed so as to remove non-immunocomplexed material. A particular washing procedure includes washing with a solution such as PBS/Tween®, or borate buffer.

To provide a detecting means, the second antibody may have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present disclosure will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

Immunohistochemistry may be useful according to the present disclosure as well. Such a detection method would require a biopsy of a sample or mastectomy from an individual suffering or suspected of suffering from cancer. This technique involves testing of both fresh-frozen and formalin-fixed, paraffin-embedded tissue blocks prepared from study by immunohistochemistry (IHC). For example, each tissue block consists of 50 mg of residual "pulverized" tissue. The method of preparing tissue blocks from these particulate specimens has been successfully used in previous IHC studies of various diagnostic and prognostic factors is well known to those of skill in the art.

Briefly, frozen-sections may be prepared by rehydrating 50 ng of frozen "pulverized" sample at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 intact cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

IV. Methods of Therapy

The present disclosure also involves, in another embodiment, the treatment of cancer. Any type of cancer may be treated, but in particular those where defects in SALL1 expression or activity exist. Thus, it is contemplated that a wide variety of tumors may be treated using SALL1 therapy, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

It is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in tumorigenesis. Specifically, the present inventors intend to provide, to a cancer cell, an expression construct capable of providing SALL1 to that cell. Because the sequence homology between the human, mouse and dog genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particular expression vectors are viral vectors such as adenovirus, adeno-associated virus, herpesvirus, vaccinia virus and retrovirus. Also contemplated are liposomally-encapsulated expression vectors.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is to contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized. For blood borne cancers, such as leukemias, a systemic route will be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way SALL1 may be utilized according to the present disclosure.

RNA-guided nucleases-mediated genome editing, based on Type II CRISPR (Clustered Regularly Interspaced Short Palindromic Repeat)/Cas (CRISPR Associated) systems, offers a new approach to alter the genome. In brief, Cas9, a nuclease guided by single-guide RNA (sgRNA), binds to a targeted genomic locus next to the protospacer adjacent motif (PAM) and generates a double-strand break (DSB). The DSB is then repaired either by non-homologous end-joining (NHEJ), which leads to insertion/deletion (indel) mutations, or by homology-directed repair (HDR), which requires an exogenous template and can generate a precise modification at a target locus. Unlike other gene therapy methods, which add a functional, or partially functional, copy of a gene to a patient's cells but retain the original dysfunctional copy of the gene, this system can remove the defect. Genetic correction using engineered nucleases has been demonstrated in tissue culture cells and rodent models of rare diseases.

Thus, the application of CRISPR/Cas9-mediated genome editing in vivo to remove mutations is eh SALL1 gene may be accomplished by injecting Cas9, sgRNA and HDR template into cells to correct a function destroying gene mutation in the SALL1 gene, thereby restoring SALL1 tumor suppressive effects.

B. Protein Therapy

Another therapy approach is the provision, to a subject, of SALL1 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

C. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present disclosure, it is contemplated that SALL1 replacement therapy could be used similarly in conjunction with chemo- or radiotherapeutic intervention. It also may prove effective to combine SALL1 gene therapy with immunotherapy, such as with an adjuvant therapy, anti-CTLA4 therapy, or PD1/PDL1 checkpoint blockage, IL-2, Trastuzumab, IDO inhibitors or PLX3397.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with a SALL1 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other, within about 6-12 hours of each other, or about 12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either SALL1 or the other agent will be desired. Various combinations may be employed, where SALL1 is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The disclosure also encompasses the use of a combination of one or more DNA damaging agents, whether radiation-based or actual compounds, such as the use of X-rays with cisplatin or the use of cisplatin with etoposide. In certain embodiments, the use of cisplatin in combination with a SALL1 expression construct is particularly contemplated.

In treating cancer according to the disclosure, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or, cisplatin. The agent may be prepared and used as a combined therapeutic composition, or kit, by combining it with a SALL1 expression construct, as described above.

Agents that directly cross-link nucleic acids, specifically DNA, are envisaged to facilitate DNA damage leading to a synergistic, antineoplastic combination with SALL1. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of SALL1 expression constructs to patients with cancer will be a very efficient method for treating the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining SALL1 therapies with chemo- and radiotherapies, it also is contemplated that combination with other gene therapies will be advantageous. For example, targeting of SALL1 and p53 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It also should be pointed out that any of the foregoing therapies may prove useful by themselves in treating a SALL1-related cancer. In this regard, reference to chemotherapeutics and non-SALL1 gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the specific methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Kits

According to the present disclosure, there are provided kits for detecting SALL1 mutations and SALL1 expression. The kit of the present disclosure can be prepared by known materials and techniques which are conventionally used in the art. Generally, kits comprises separate vials or containers for the various reagents, such as probes, primers, enzymes, antibodies, etc. The reagents are also generally prepared in a form suitable for preservation by dissolving it in a suitable solvent. Examples of a suitable solvent include water, ethanol, various buffer solutions, and the like. The various vials or containers are often held in blow-molded or injection-molded plastics.

VI. Examples

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1: Materials & Methods

Human Samples and Cell Lines.

Tumor samples were obtained from breast cancer patients treated at the Department of Surgery, Saint Louis University from 2004 to 2010 who have given informed consents for enrollment in a prospective tumor procurement protocol approved by the Saint Louis University Institutional Review Board. Paired fresh tumor tissues and normal breast tissues were obtained perioperatively and snap frozen in liquid nitrogen (N=46). In addition, fresh-frozen metastatic cutaneous melanoma tumor tissues were also collected as controls for this study. Breast tumor cell lines (human MDA, MCF7, BC80, 31, 30, 29, 16, and murine 4T1 and E0771), Melanoma cell lines (Mel1938, Mel1586, Mel1860, Mel1363, Mel1526 and Mel1628, and murine B16F0), prostate cell line PC3 and DU145, colon cancer cell line SW480 and lymphoma L428 and L504, as well as normal breast cells and fibroblast cells, were either obtained from the American Tissue Culture Collection (ATCC) or established by the inventors, and maintained in RPMI 1640 medium containing 10% fetal calf serum (FCS) and penicillin-streptomycin (Invitrogen, Inc. San Diego, Calif.).

Plasmid Constructs.

Full length flu-tagged SALL1 wild-type and mutant constructs cloned into pcDNA3.1 were prepared as previously described (23). Point mutants were created by PCR-mediated site directed mutagenesis using QuikChange (Stratagene). The amplified PCR products were cloned into lentivirus vector pCDH-CMV-EF1-GFP. The nucleotide sequences of all constructs were verified by DNA sequencing.

Immunohistochemical Staining of SALL1 and Quantification Method.

The cell populations of SALL1$^+$ cells in cancer and normal tissues (frozen sections) were determined using immunohistochemical staining with the Histostain®-Plus 3rd Gen IHC Detection Kit (Invitrogen, CA), as described previously (Ma et al., 2012 and Ye et al., 2013). Immunohistochemical reactions were performed using either mouse monoclonal or rabbit polyclonal antibodies against SALL1 at dilution of 1:1500. Controls were performed by incubating slides with the isotype control antibody instead of primary antibodies, or second antibody alone. SALL1$^+$ cells in tissues were evaluated manually using a computerized image system composed of a Leica ICC50 camera system equipped on a Leica DM750 microscope (North Central Instruments, Minneapolis, Minn.). Photographs were obtained from 20 randomly selected areas within the tumor tissues of 10 cancer nest areas and 10 cancer stroma areas at a high-power magnification (400×). Both cancer nest and stroma areas were counted and summed, and the means of positive cell numbers per field reported.

Reverse-Transcription PCR® Analysis.

Total RNA was extracted from tumor or normal tissues and cell lines using Trizol reagent (Invitrogen), and cDNA was transcribed using a SuperScript II RT kit (Invitrogen), both according to manufacturers' instructions. SALL1, 2, 3 and 4 mRNA expressions were determined by reverse-transcription PCR® using specific primers, and mRNA levels in each samples were normalized to the relative quantity of Glyceraldehyde-3-phosphate dehydrogenase (GAPDH) as previously described (Peng et al., 2005 and Peng et al., 2007). All samples were run in triplicate. The primers for each gene used were as following:

```
SALL1: 5' TGATGTAGCCAGCATGT 3'      (SEQ ID NO: 3)
and
       5' AAAGAATTCAGCGCAGCAC 3'    (SEQ ID NO: 4)

SALL2: 5' CCAAGAGTAAAGCGGATGAGA 3'  (SEQ ID NO: 5)
and
       5' AGTAAGCAGTGCCCAACTCG 3'   (SEQ ID NO: 6)

SALL3: 5' TGGGCCTTCGCTTACTAAAG 3'   (SEQ ID NO: 7)
and
       5' ACAGCAGTGGCAGCTGAAG 3'    (SEQ ID NO: 8)

SALL4: 5' AGCAGCCTCAGCAGCTACC 3'    (SEQ ID NO: 9)
and
       5' AAGAACTCGGCACAGCATTT 3'   (SEQ ID NO: 10)
```

Cell Growth and Functional Proliferation Assay.

Tumor cell lines were plated at 2×10$^4$/well in 24 wells and transfected with one of the following plasmids: pcDNA3.1-SALL1, pcDNA3.1-SALL4, and pcDNA3.1. Cell growth was evaluated at different time points by counting cell numbers. Proliferation assays were performed as previously described (Peng et al., 2005 and Peng et al., 2007). In brief, different numbers of tumor cells (2×10$^4$, 5×10$^4$, or 1×10$^5$) transfected with or without the related genes were cultured in 96-well plates in cell assay medium containing 2% FCS. After 56 hours of culture, [$^3$H]-thymidine was added at a final concentration of 1 µCi/well, followed by an additional 16 hrs of culture. The incorporation of [$^3$H]-thymidine was measured with a liquid scintillation counter.

Cell Cycle and Apoptosis Assays.

Transfected cells were cultured for 72 hours and apoptosis was analyzed after staining with PE-labeled Annexin V and 7-AAD (BD Biosciences, San Diego, Calif.). For cell cycle analysis, transfected cells were fixed with 70% ethanol overnight, washed with PBS and incubated with propidium iodide (10 µg/ml) and RNase A (100 µg/ml). Untransfected cells served as controls. All the stained cells were analyzed on a FACSCalibur (BD Bioscience) and the data were analyzed with FlowJo software (Tree Star, Ashland, Oreg.).

Senescence associated β-Galactosidase (SA-β-Gal) staining.

Senescence associated β-Galactosidase (SA-β-Gal) activity in tumor cells was detected as previously described (30, 33). Briefly, tumor cell lines were transfected with or without plasmids and cultured for 3 or 5 days. Cells were washed in PBS (pH 7.2), fixed in 3% formaldehyde, and followed to incubate overnight at 37° C. with freshly prepared SA-β-Gal staining solution (1 mg/ml X-gal, 5 mM $K_3Fe[CN]_6$, 5 mM $K_4Fe[CN]6$, 2 mM $MgCl_2$ in PBS at pH 6.0). The stained cells were washed with $H_2O$ and examined with a microscope. For some experiments, SA-β-Gal$^+$ populations were determined in the transfected tumor cells in the presence of following various inhibitors or combined transfection with shRNAs: ATM inhibitor KU55933 (20 µM, Tocris Bioscience); mTOR inhibitor Rapmycin (5 µM, Sigma); MAPK inhibitors U0126 (10 µM), SB203580 (10 µM) and SP600125 (10 µM), or PI3 Kinase inhibitor Wortminnin (10 µM) (Calbiochemistry), or transfection with shRNAs against p38, ERK and mTOR, for 3 or 5 days. The treated tumor cells were then detected for SA-β-Gal expression.

Western-Blotting Analysis and Protein Interaction Assays.

Breast cancer cells transfected with or without plasmids pcDNA3.1-SALL1 or pcDNA3.1-mSALL1, were cultured for 0, 24 hrs, 48 hrs and 72 hrs. Whole cell lysates were prepared for western blotting. The antibodies used in western blotting are as follows: anti-ERK, anti-phospho-ERK, anti-p38, anti-phospho-p38, anti-JNK, anti-phospho-JNK, anti-phospho-p53 (ser15), anti-mTOR, anti-phospho-mTOR; anti-P70S6K, anti-phospho-P70S6K; anti-4E-BP1, anti-phospho-4E-BP1, anti-PTEN, anti-phospho-PTEN and anti-GAPDH rabbit polyclonal antibodies (Cell Signaling Technology, Danvers, Mass.).

Protein interaction analysis of NuRD complex members with SALL1 (2-137) was performed as previously described (Lauberth et al., 2007 and Lauberth & Rauchman, 2006). In brief, MCF-7 breast tumor cells were transfected with plasmids pEBG-SALL1, pEBG-SALL1-S2A, and pEBG-SALL1-S2E, and allowed to expression GST-SALL1 fusion proteins for 48-72 hrs. Cells were incubated for 1 hr on ice in lysis buffer (1% Triton X-100, 200 mM sucrose, 50 mM Tris pH 7.4, plus protease cocktail) and the cell suspension was disrupted by sonication. GST-SALL1 fusions and associated protein complexes were isolated by precipitation of 50 µg of total protein with glutathione-Sepahrose beads (Amersham Biosciences) for 2 hrs at 4° C. Protein pull-downs were separated by SDS-PAGE and proteins detected by western blot. Primary antibodies were all used at 1:1000 dilution and included: rabbit anti-SALL1 (Kiefer et al., 2002), rabbit anti-Mta2 (Abcam, ab 8106), mouse anti-RbAp48 (GeneTex, GTX 70237), rabbit anti-Hdac1 (Abcam, ab 19845), rabbit anti-Mbd3 (Abcam, ab 157464). Secondary antibodies were used at 1:10,000 included: goat anti-rabbit (Sigma, A0545) and rabbit anti-mouse (Jackson immune Research 315-035-048).

Flow Cytometry Analysis.

The expression of DNA damage response markers on tumor cells were determined by FACS analysis after staining with anti-human specific antibodies conjugated with either PE or FITC. These human antibodies included: anti-phosphorylated H2Ax, anti-phosphorylated p53 bp, and anti-phosphorylated ATM, which were purchased from Cell Signaling Technology or BD Biosciences. All stained cells were analyzed on a FACSCalibur flow cytometer (BD Bioscience) and data analyzed with FlowJo software (Tree Star).

Cell migration and wound healing assay. Breast cancer E0771 and MCF-7 tumor cells transfected with Lenti-SALL1, Lenti-mSALL1 or vector, were plated in 6-well plates and grown to confluence. A wound area was generated by scraping cells with a 200 µl pipette tip across the entire diameter of the dish and extensively rinsed with the medium to remove all cellular debris. Low-serum RPMI 1640 with mitomycin (2 µg/ml) was then added to inhibit cell proliferation during the experiment and the closing of the wound was observed at different time points.

Lentivirus-shRNA Generation and Gene Knockdown in Tumor Cells.

The methods for design and construction of shRNA specific for ERK1, ERK2, P38a, JNK1 and mTOR or scrambled lenti-shRNAs, and generation of recombinant lentivirus carrying GFP and shRNA, have been described previously (Peng et al., 2005 and Peng et al., 2007). For virus transfection, concentrated lentiviral supernatant with a multiplicity of infection (MOI) of 5-10 in a total volume of 0.5 ml culture medium was added to the tumor cells growing in 24 well plates containing 8 µg/ml polybrene (Sigma), and then centrifuged at 1000×g for 1 hr at room temperature. Tumor cells were sorted into GFP$^+$ and GFP$^-$ cells with a FACS ARIA sorter at 3 or 4 days post-transfection. The sorted cells (GFP$^+$ and GFP$^-$) were then transfected with or without pcDNA3.1-SALL-1, and induction of senescence was determined.

In Vivo Tumorigenesis and Metastasis Studies.

NOD-scid IL2Rgamma$^{null}$ (NSG, 6-8 weeks) immunodeficient mice were purchased from The Jackson Laboratory and maintained in the institutional animal facility. All animal studies have been approved by the Institutional Animal Care Committee. For tumorigenesis studies, mouse E0771 (2×10$^5$/mouse) and B16F0 (1×10$^5$/mouse) tumor cells infected with lentivirus carrying SALL1, mSALL-1 or vector, were subcutaneously injected into NSG mice. Five to ten mice were included in each group. Tumor size was measured with calipers every 2-3 days. Tumor volume was calculated on the basis of two-dimensional measurements. At the end of experiments, the mice were sacrificed and tumors were isolated and weighted. Furthermore, tumor tissues were embedded into OCT and prepared for cryostat sections (4-8 µm), and SA-β-Gal expression was assayed, as described above.

For tumor metastasis studies, lentivirus-transfected E0771 tumor cells were incubated with 100 µg/ml of VivoTag®680 XL (PerkinElmer) for 30 minutes. Stained tumor cells were washed and then injected intravenously into the tail vein (5×10$^4$/mouse in 200 µl of buffered saline) into NSG mice. Five to ten mice were included in each group. Mice were imaged with an In Vivo Spectrum Imaging System (IVIS) (Caliper Life Science) at 120 min, and 1, 3, 5, 7, 10, 14, 17 and 19 days post injection. The appropriate filter set for VivoTag®680 XL imaging of 665 nm excitation and 688 nm emission was used. Mice were imaged in the dorsal, right lateral and ventral positions at all the time points. Livers and lungs were harvested at 19 days post injection and stained with 15% black India ink as described previously (Sato et al., 2004). Visible lung and liver surface macrometastatic appeared as white spots and were counted using a dissecting microscope. Lungs were collected and fixed in 10% formalin. For tissue morphology and metastasis evaluation, liver and lung tissues were embedded into OCT and frozen sections (4-8 µm) were prepared and stained with hematoxylin and eosin (H & E).

Statistical Analysis.

Statistical analysis was performed with GraphPad Prism5 software. Unless indicated otherwise, data are expressed as mean±standard deviation (SD). For public database analysis, The Cancer Atlas (TCGA) normalized log 2 transformed breast cancer Argilent microarray expression data sets were downloaded from the cBioPortal (world-wide-web at cbioportal.org) and used to compare SALL1 mRNA expression among the different breast cancer subtypes and solid normal tissues (Cancer Genome Atlas N, 2012). The Mann-Whitney U test was utilized for statistical analysis of association between SALL1 expression and breast cancer subtypes. P valve<0.05 was considered statistically significant. For multiple group comparison in vivo studies, the one-way analysis of variance (ANOVA) was used, followed by the Dunnett's test for comparing experimental groups against a single control. For single comparison between two groups, paired Student's t test was used. Non-parametric t-test was chosen if the sample size was too small and did not fit a Gaussian distribution.

Example 2—Results

SALL1 Expression is Down-Regulated in Human Breast Cancer Cell Lines and Tissues.

Figure 1B:
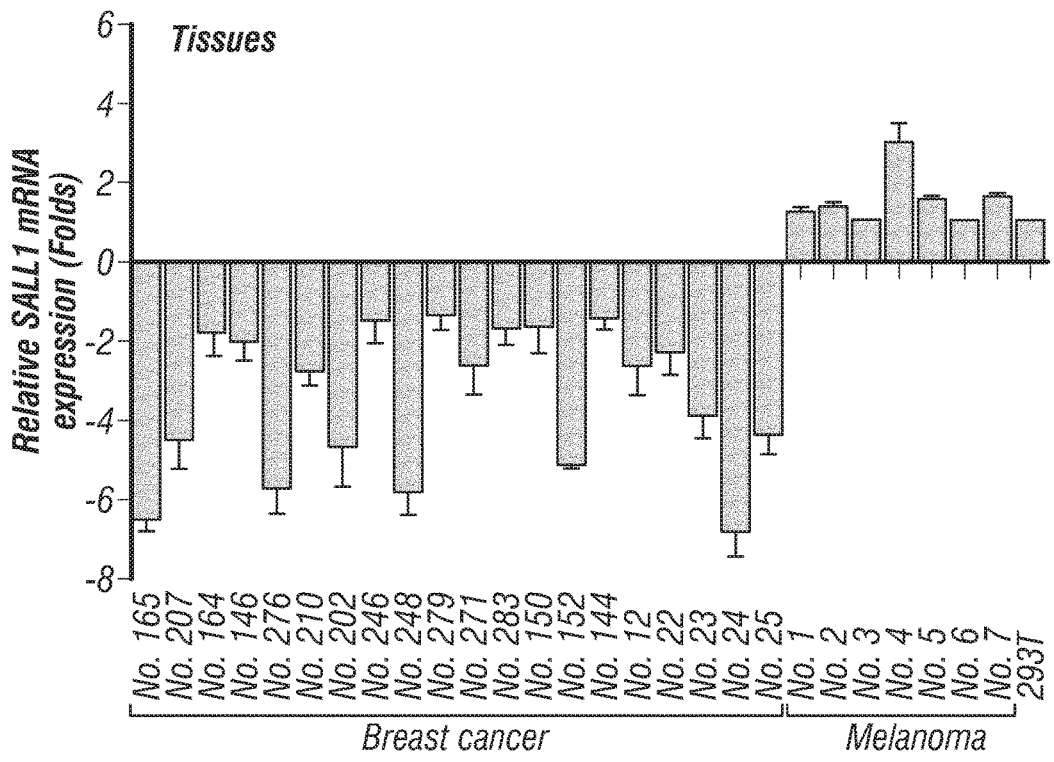

Increasing evidence suggests that SALL4 regulates stem cell differentiation and leukemogenesis (Yang et al., 2008 and Li et al., 2013), but little is known about the role of SALL1 in tumor pathogenesis. A recent report identified that SALL1 is as a candidate tumor suppressor in human breast cancer, using an in vivo RNAi screen strategy (Wolf et al., 2014). The inventors investigated whether SALL1 could function as a tumor suppressor and dissected the molecular mechanism by which it regulates human breast cancer. They first determined SALL1 gene expression levels in breast cancer cell lines using Real-time PCR analyses. In parallel, SALL1 expression in cancer cell lines from other types of cancers (melanoma, prostate cancer, colon cancer and lymphoma), as well as in normal fibroblasts and 293T cells were also determined. The inventors observed markedly elevated SALL1 gene expression in all melanoma cell lines and moderate gene expression in normal fibroblasts and 293T cells (FIG. 1A). In contrast, SALL1 gene expression levels in all the tumor cell lines from breast cancer, prostate cancer, colon cancer and lymphoma were significantly down-regulated. These results were confirmed in human breast and melanoma tumor tissues and in normal breast tissues as well, showing down-regulation of SALL1 gene in normal breast and breast cancer tissues (FIG. 1B).

Figure 1C:
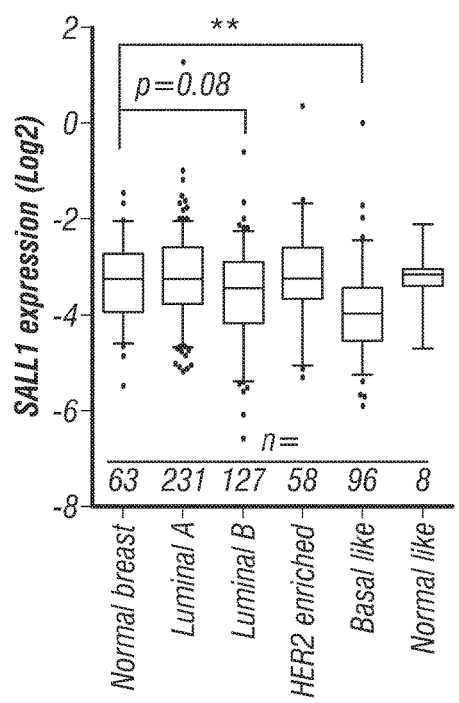
Figure 1D:
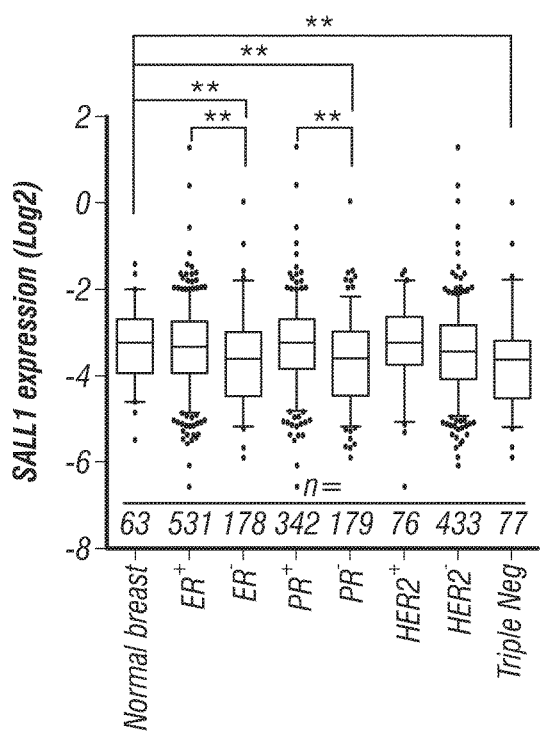
Figure 1E:
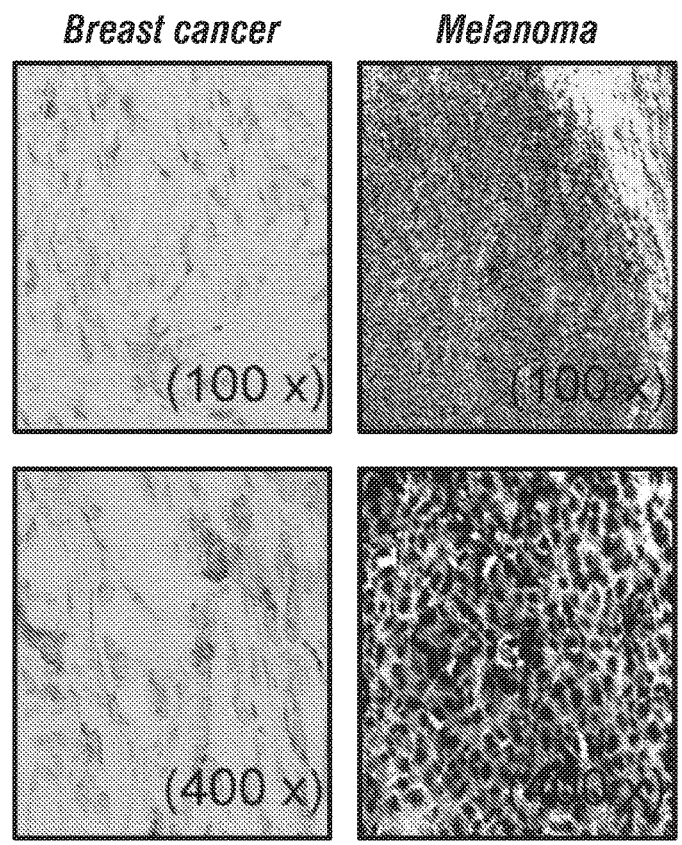
Figure 1F:
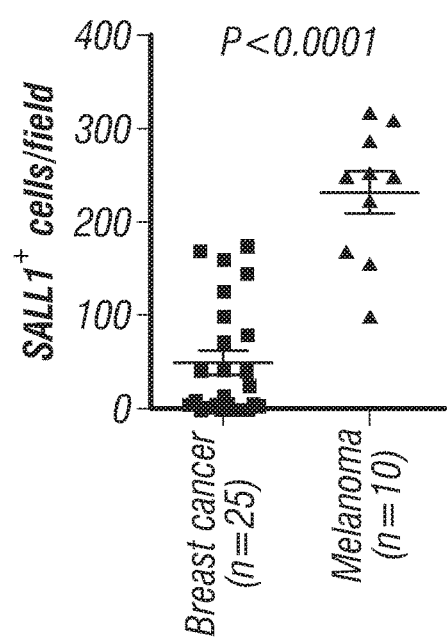
Figure 1G:
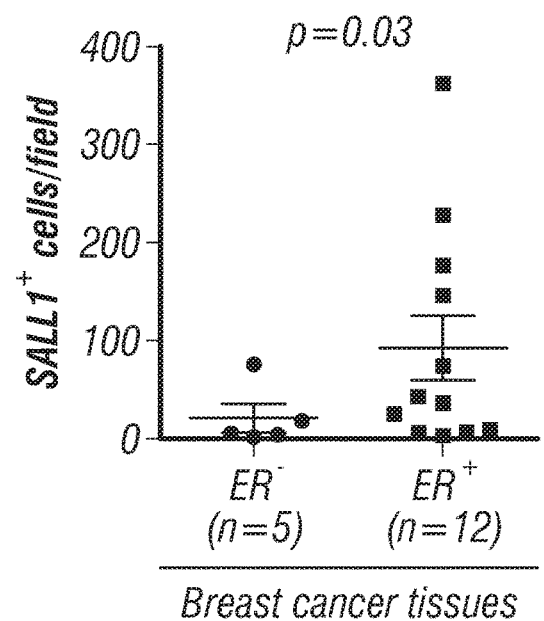
Figure 1H:
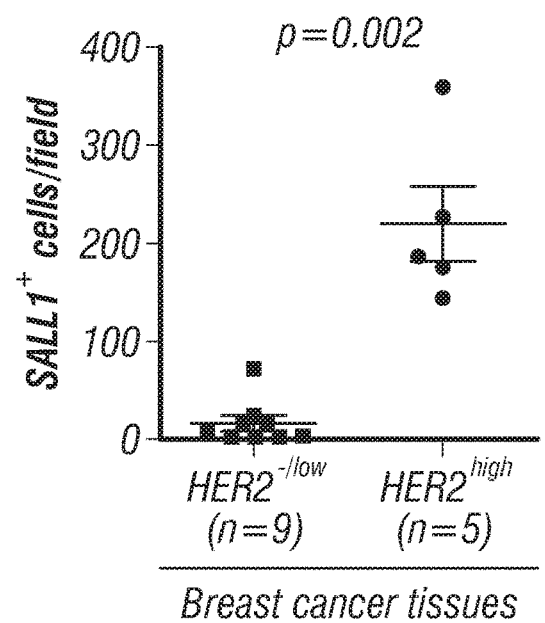

Clinically breast cancers can be classified into several distinct subtypes based on the histopathology and molecular characteristics which are associated with the therapeutic options and prognostic outcomes. To further investigate the association of SALL1 gene expression with breast cancer subtypes, the inventors utilized The Cancer Atlas (TCGA) normalized $log_2$ transformed breast cancer Argilent microarray expression data sets downloaded from cBioPortal (world-wide-web at cbioportal.org) for their studies (Cancer Genome Atlas N, 2012). Breast cancers have been designated as luminal A, luminal B, HER2 enriched, basal like and normal like, five important categories based on gene expression profiles (Fan et al., 2006). The inventors found that a substantial decrease of SALL1 expression in the basal like breast cancer compared with that in normal breast tissue (p<0.001) (FIG. 1C). Furthermore, the inventors also determined whether SALL1 had different expression in breast cancer patients with different hormone receptors, estrogen receptor (ER) and Progesterone receptor (PR), or Epidermal growth factor receptor 2 (HER2) expression statuses (FIG. 1D). The analysis revealed that there was significant lower expression of SALL1 in the ER$^-$ breast cancer than that in ER$^+$ cancer tissues and the normal breast tissues (p=0.006 and p=0.008, respectively). Similarly the SALL1 expression was lower in PR$^-$ breast cancer than that in PR$^+$ breast cancer or normal breast tissues (p<0.001 and p=0.006, respectively). Importantly, the inventors also found a significant lower expression level of SALL1 in triple negative breast cancer tumors (ER$^-$,PR$^-$, and Her2$^-$) compared with that in normal breast tissues (p=0.0021). To further investigate the SALL1 expression in human breast cancer, the inventors we determined the SALL1$^+$ cell numbers in cancer tissues from breast and melanoma cancer patients, using immunohistochemical staining analyses. Consistent with the gene expression results (FIG. 1B), the inventors found that melanoma tumor tissues contained larger numbers of SALL1$^+$ cells (mean 232/field), while in breast cancer tissues, the SALL1$^+$ cells were low (mean 50/field) (FIGS. E and F). Notably, SALL1$^+$ cell numbers in ER$^-$ patients were significant lower than those in ER$^+$ patients (FIG. 1G). Interestingly, SALL1$^+$ cell population in HER2$^+$ patients was much higher than that in HER2$^-$ patients (FIG. 1H). Recent studies have shown that SALL4 is involved in the leukemogenesis and a marker for hepatoblastoma and non-small cell lung carcinoma (Li et al., 2013; Gnemmi et al., 2013; Cao et al., 2009; Ushiku et al., 2010). The inventors therefore determined SALL4 gene expression in breast cancer cell lines and primary cancer tissues using Real-time PCR analyses. In contrast to SALL1 gene expression, the inventors found significantly high expression of SALL4 in both breast cancer cell lines and primary cancer tissues, suggesting that SALL1 and SALL4 may have distinct functional roles in the regulations of breast cancer (FIGS. 8A-B). Collectively, these results suggest that SALL1 gene expression is significantly down-regulated in human breast cancer cells and cancer tissues, especially in triple-negative breast cancer, which may play critical role in the pathogenesis of human breast cancer.

SALL1 Over-Expression in Breast Cancer Cells Inhibits Tumor Cell Growth and Proliferation, and Promotes Cell Cycle Arrest.

Given that the inventors' studies showed SALL1 gene is down-regulated in breast cancer, and that it could be a tumor suppressor (Wolf et al., 2014), they reasoned that SALL1 may directly influence cancer cell growth and functions. To test this possibility, SALL1 gene was transfected into human and murine breast cancer cell lines MCF7 and E0771 (both with no or minor expression of SALL1) for the gain-of-function studies. Prostate cancer cell line PC-3 (SALL1 lowly expressed) and melanoma cell line B16F0 (SALL1 highly expressed) were included as controls. Tumor cell growth and proliferation were determined using the cell growth curve and [$^3$H]-thymidine incorporation assays. As shown in FIGS. 2A-B, transfection of SALL1, but not SALL4 or vector in MCF-7, E0771 and PC-3 tumor cells significantly inhibited the cell growth and proliferation. However, over-expression of SALL1 in B16F0 melanoma cells did not affect cell growth and proliferation. These results further suggest that SALL1 directly inhibit breast cancer cell growth, but it may have different functions in the other types of cancers.

Figure 2C:
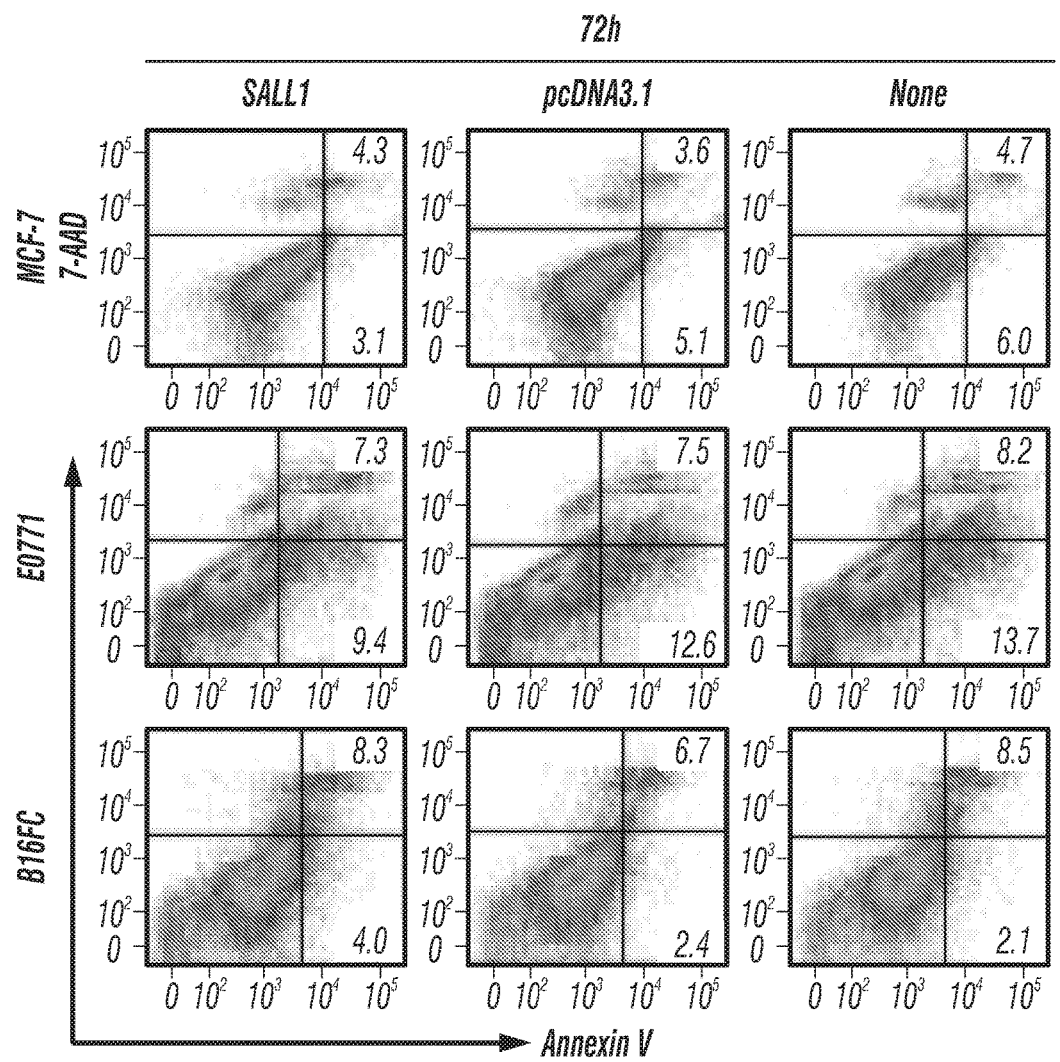
FIGS. 2A-D. Over-expression of SALL1 in breast cancer cells inhibits tumor cell growth and proliferation, and promotes cell cycle arrest.
Figure 2:
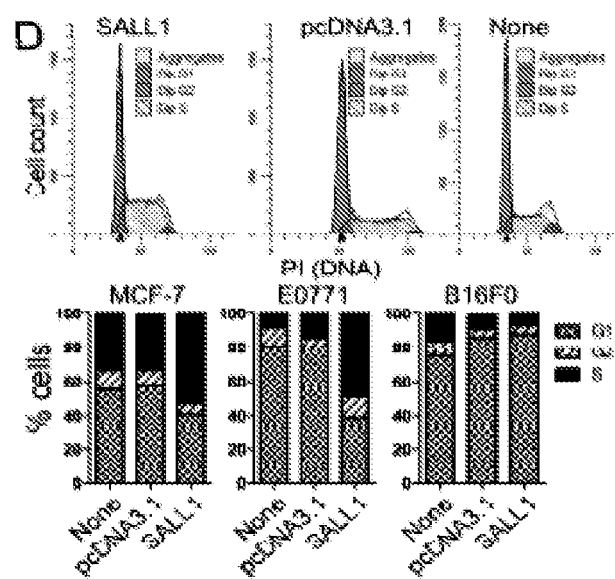
Figure 9:
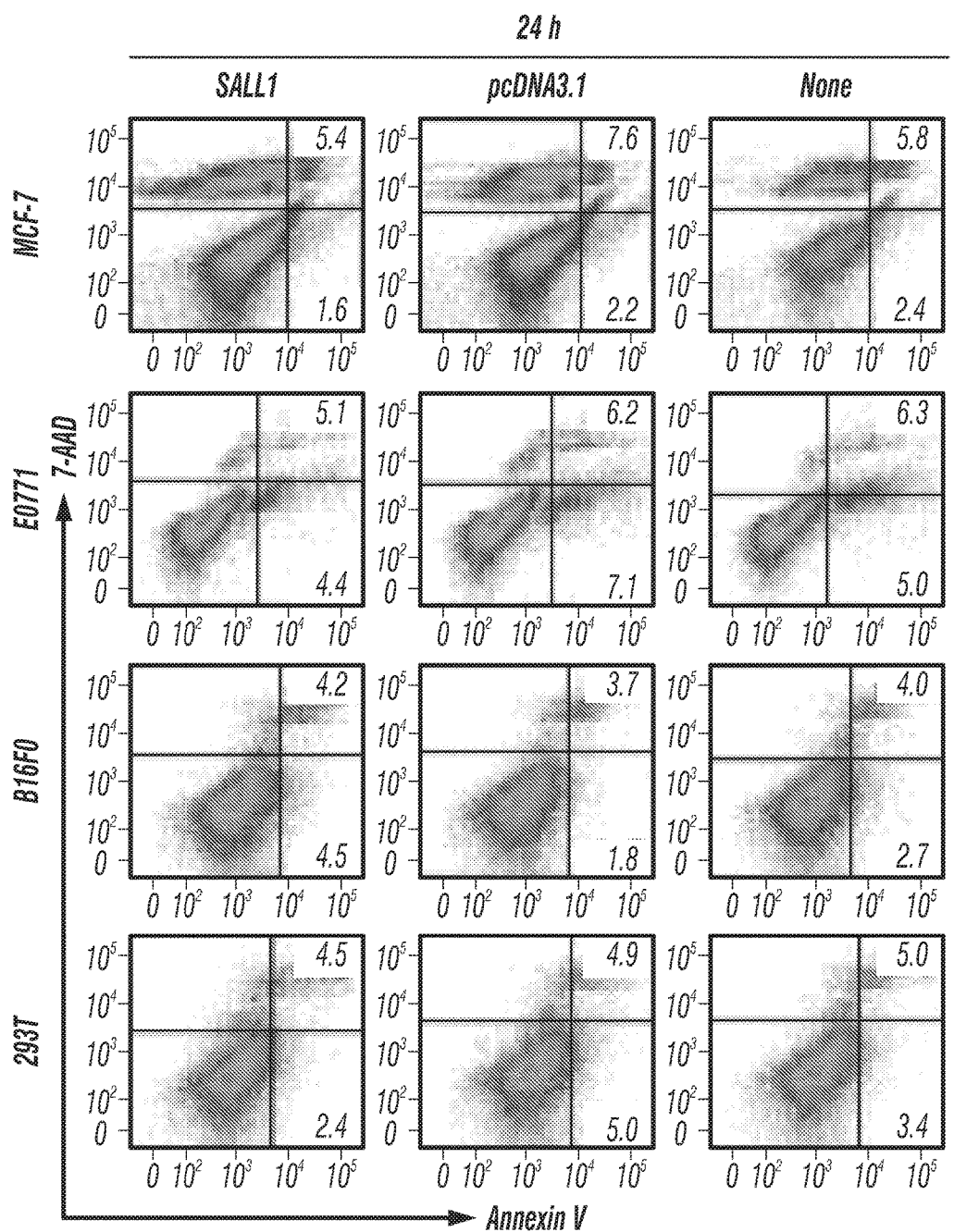
FIG. 9. The inhibition of breast cancer cell proliferation and growth mediated by SALL1 expression is not due to the induction of apoptosis. Transfected breast cancer and melanoma cells were cultured for additional 24 hours. Apoptosis in transfected tumor cells was analyzed after staining with PE-labeled Annexin V and 7-AAD. 293 T cells were included as a control. Data shown are representative of three independent experiments with similar results.

Suppression of tumor cell proliferation and growth mediated by SALL1 expression could be due to the induction of apoptosis or cytolysis in the tumor cells. The inventors therefore measured apoptosis and cell death in SALL1-transfected breast tumor cells. They found that breast tumor cells MCF7 and E0771 in medium alone or transfected with control vector contained some apoptotic cells (around 10% in MCF-7 and 20% in E0771). However, overexpression of SALL1 in cancer cells did not induce increased apoptosis or cell death in either breast cancer cell lines (FIG. 2C and FIG. 9). In parallel, the inventors studied the cell cycle distribution of the breast cancer cells transfected with SALL1. SALL1 transfection in both MCF-7 and E0771 cells significantly induced cancer cells to arrest in S phase and decrease in G0/G1 phase (FIG. 2D). Notably, transfection of SALL1 in melanoma B16F0 cells induced neither cell apoptosis nor cell cycle arrest. Collectively, these data suggest that overexpression of SALL1 gene in breast cancer strongly suppresses tumor growth and proliferation, as well as induces cell cycle arrest, which is mechanistically independent of apoptosis or cytolysis in tumor cells.

SALL1 Over-Expression in Breast Cancer Cells Induces Tumor Cell Senescence.

Figure 10:
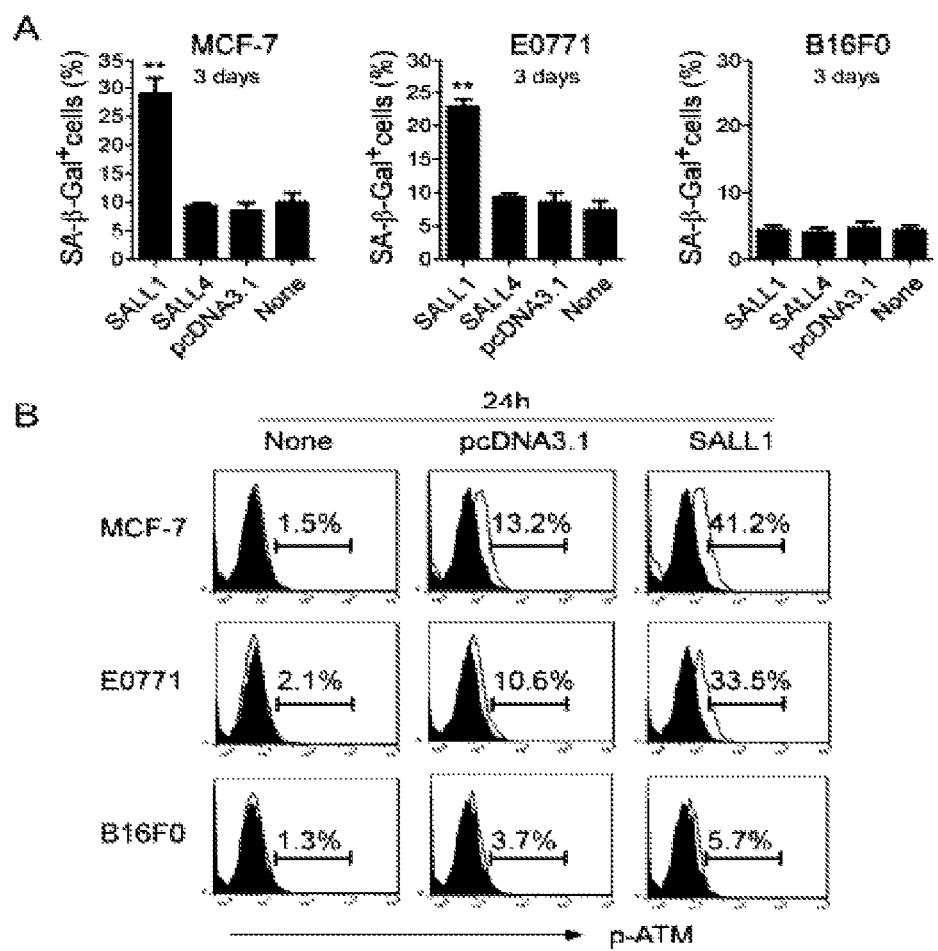
FIGS. 10A-B. SALL1 over-expression in breast cancer cells induces tumor cell senescence.

Senescent human cells have permanent growth arrest, which could occur due to telomere shortening or DNA damage response (d'Adda di Fagagna et al., 2003 and Herbig et al., 2004). The inventors therefore reasoned that senescence induction mechanism might be involved in the suppressed cell growth and proliferation mediated by overexpression of SALL1 in breast cancer cells. In addition to cell cycle arrest and morphologic characteristics, SA-β-Gal is the first biomarker used to identify senescent human cells (Ye et al., 2013 and Ye et al., 2012). They observed that transfection of SALL1 in MCF-7, E0771 and PC-3 tumor cells significantly increased SA-β-Gal$^+$ cell populations in these cells, indicating the induction of tumor cell senescence (FIGS. 3A-B and FIG. 10A). In contrast, these tumor cells transfected with SALL4 or control vector did not induce increased SA-β-Gal expression. In addition, the inventors did not observe increased senescent cell populations in melanoma B16F0 cells after over-expression of SALL1.

The induction of DNA damage is the key molecular process in senescent cells, which could be induced by telomere erosion and/or other forms of stress (Ye et al., 2012). The nuclear kinase ataxia-telangiectasia mutated protein (ATM) is the chief inducer of the DNA-damage response. The inventors thus determined whether induction of ATM-associated DNA damage is the main trigger for SALL1-induced senescence in breast tumor cells (Rodier et al., 2009 and Guo et al., 2007). As expected, over-expression of SALL1 significantly induced phosphorylated activation of ATM in MCF-7 and E0771 cancer cells (FIG. 3C and FIG. 10B). In addition, the inventors further investigated the other key DNA damage response proteins involved in the induction of senescence in breast tumor cells mediated by SALL1 expression. These proteins include ATM substrates γ-H2AX and 53BP1, as well as the downstream target checkpoint kinase 2 (CHK2) (Guo et al., 2007 and Rodier et al., 2009). The inventors observed that transfection of SALL1, but not SALL4 or control vector also significantly induced phosphorylation of γ-H2AX, 53BP1 and CHK2 in MCF-7 and E0771 cells (data not shown). To confirm the involvement of ATM-associated DNA damage in SALL1-mediated breast cancer cell senescence, the inventors next determined whether one can prevent the SALL1-mediated senescence in breast cancer cells through the functional blockage of ATM-induced DNA damage using the loss-of-function approach with specific pharmacological ATM inhibitor KU55933. As shown in FIG. 3D, treatment of breast cancer MCF-7 and E0771 cells with KU55933 dramatically suppressed the phosphorylation of ATM in SALL1-transfected tumor cells and prevented the senescence induction in tumor cells, further confirming the involvement of the ATM-associated DNA damage response in SALL1-induced tumor cell senescence. These data provide the first evidence that suppression of breast cancer growth and proliferation mediated by SALL1 expression is due to the induction of tumor cell senescence.

SALL1 Recruits NuRD in Breast Cancer Performing a Tumor Suppressor Function.

Figure 11:
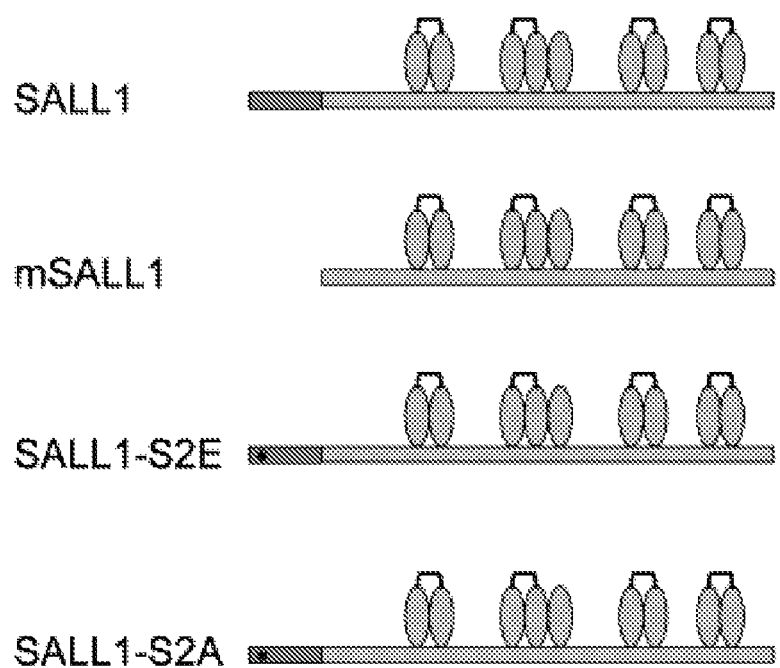
FIG. 11. SALL1 proteins expressed in transfected breast cancer cells. Wild-type SALL1 is shown at the top. Red represents the 12 amino acid region that mediates NuRD complex recruitment. Blue ovals are C2H2 zinc fingers. In mutant mSALL1, the 12 amino acid NuRD recruitment domain is deleted. In SALL1-S2E, the serine at position 2 is mutated to a glutamic acid. This phosphomimetic mutation disrupts NuRD recruitment, similar to the deletion mutant. In SALL1-S2A, the serine at position 2 is mutated to an alanine. This substitution prevents the inactivating serine phosphorylation, thereby enhancing Sall1 mediated transcriptional repression.

The inventors' previous studies have shown that endogenous SALL1 binds to the NuRD complex to regulate gene transcription and specific developmental processes (Kiefer et al., 2010; Kiefer et al., 2010; Lauberth et al., 2007 and Lauberth & Rauchman, 2006). The inventors further identified a highly conserved 12-amino acid motif in the SALL1 protein that is sufficient for the recruitment of NuRD (Lauberth & Rauchman, 2006). Importantly, increasing evidence suggests that the NuRD complex plays an essential role in regulating oncogenesis and metastasis programs of breast cancer (Lai & Wade, 2011; Wang et al., 2009; Fujita et al., 2003 and Fu et al., 2011). The inventors therefore hypothesized that SALL1-mediated suppression of breast cancer growth and proliferation, and induction of tumor cell senescence may also be through the recruitment of the NuRD complex. To test this hypothesis, they first transfected a mutated SALL1 encoding a protein in which the conserved 12-amino acid peptide motif that specifically binds to NuRD was deleted, into breast cancer cells and determined the capacity for the senescence induction (FIG. 11). Consistent to the above results, transfection of full-length SALL1 into MCF-7 and E0771 breast cancer cells significantly induced tumor cell senescence (around 40%) and promoted cell cycle arrest in S phase in 3 days (FIGS. 4A-B). However, transfection of the mutated SALL1 in the breast cancer cells did not have any effects on cell senescence and cell cycle, similar to that of control vector, suggesting that breast cancer cell senescence mediated by SALL1 gene depends on NuRD recruitment.

In their efforts to identify the relationship and direct interactions between SALL1 and NuRD, the inventors have previously demonstrated that protein kinase C phosphorylates serine 2 of the SALL1 repression motif regulates the association with NuRD (Lauberth et al., 2007). Furthermore, the inventors showed that substitution of the serine with a glutamic acid (SALL1-S2E, phosphomimetic) significantly abolished the effect on NuRD recruitment and repression activity; whereas mutating the serine to an alanine (SALL1-S2A) modestly increased the transcriptional repression (Lauberth et al., 2007 and Lauberth & Rauchman, 2006). The inventors next utilized SALL1 constructs with these two separation-of-function mutations to test its effects on senescence induction in breast cancer cells (FIG. 11). As they expected, transfection of SALL1-S2E into MCF-7 and E0771 breast cancer cells lost the ability to induce tumor cell senescence. In contrast, transfection of SALL1-S2A into tumor cells significantly augmented senescence induction in both cell lines compared with that of wild-type SALL1-transfected tumor cells (FIGS. 4C-D). To confirm the physical interaction of SALL1 with the NuRD complex in cancer cells, the inventors transfected MCF-7 breast cancer cells with GST fusions of full-length wild-type SALL1, or SALL1-S2A and SALL1-S2E. GST-SALL1 fusion proteins were isolated on glutathione-Sepharose beads. Western-blot assays were then performed to determine the expression of components of the NuRD complex, including MTA2, RbAp 46/48, HDAC1 and MBD3, after SALL1 and GST pulldown (Lauberth et al., 2007 and Lauberth & Rauchman, 2006). Transfection of the three fusion constructs equivalently expressed SALL1 protein (FIG. 4E). Expression of wild-type SALL1 and SALL1-S2A in MCF-7 tumor cells recruited the endogenous NuRD complex components. However, GST-SALL-S2E did not pulldown NuRD components even though it is expressed at a level comparable to wild-type SALL1. Collectively, these results clearly indicate that SALL1 recruits NuRD in breast cancer cells resulting in suppression of tumor growth and proliferation, and induction of tumor cell senescence.

SALL1 Induces Selective Modulation of MAPK p38 and ERK1/2, and mTOR Signaling Pathways in Breast Cancer Cells.

Figure 12:
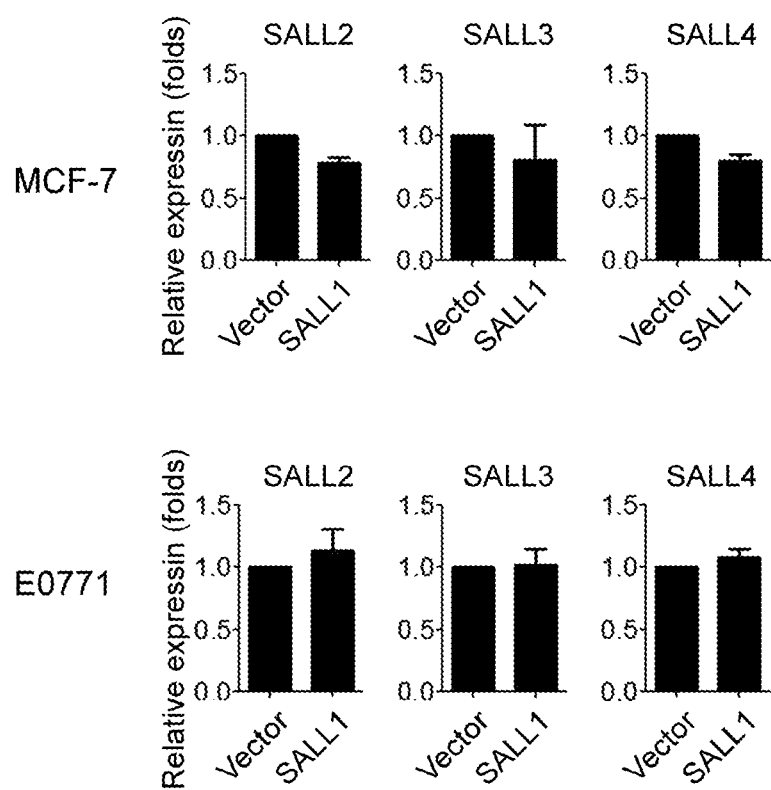
FIG. 12. Real-time PCR analyses of mRNA expression levels of the other SALL family members in breast cancer cells after transfection with SALL1. MCF7 and E0771 tumor cells were transfected with SALL1 for 24 hours and then RT-PCR was performed. The expression level of each gene was normalized to GAPDH expression and adjusted to the levels in vector-transfected tumor cells. Data show mean±SD from three independent experiments with similar results.

Besides the involvement of NuRD complex recruitment, the inventors next determined whether SALL1 could alter the expression of other members in the SALL family mediating breast cancer growth suppression (Lauberth et al., 2007 and Lauberth & Rauchman, 2006). The inventors' results showed that transfection of SALL1 in both MCF-7 and E0771 cells did not change the gene expression levels of SALL2, SALL3 and SALL4 at different time points using Real-time PCR analyses (FIG. 12). Studies from the inventors' group and others also suggested that SALL1 regulates Wnt signaling involvement in developing tissues (Kiefer et al., 2010 and Sato et al., 2004). However, the inventors did not observe the activation of Wnt signaling in breast cancer MCF-7 and E0771 cells induced by SALL1 transfection (data not shown). These results suggest that SALL1-mediating signaling in tumor cells may be different from that in the regulation of organ development.

MAPK signaling pathways play a major role in regulating cell cycle re-entry and oncogenic ras-induced senescence (Wang et al., 2002 and Kwong et al., 2009). It has been reported that ERK1/2 and p38 activation can induce p21-dependent G1 cell cycle arrest (Todd et al., 2004). The inventors' recent studies further demonstrated that MAPK ERK1/2 and p38 signaling controls the molecular process of human $CD4^+$ $CD25^{hi}FoxP3^+$ Treg-induced responder T cell senescence (Ye et al., 2012). The inventors therefore explored whether SALL1-induced breast cancer cell cycle S phase arrest and conversion of cancer cells into senescent cells involved MAPK signaling modulation. They first determined the activation and phosphorylation of MAPKs, including ERK1/2, p38 and JNK in breast cancer cells transfected with SALL1 using Western blot analyses. They found that transfection of SALL1 but not mutated SALL1 selectively activated ERK1/2 and p38, but not JNK, resulting in significantly enhanced phosphorylation of ERK1/2 and p38 in both MCF-7 and E0771 breast cancer cells (FIG. 5A). To further determine the role of ERK1/2 and p38 signaling in controlling the molecular process of SALL1-induced senescence in breast cancer cells, the inventors utilized the loss-of-function strategies with specific pharmacological inhibitors and lentivirus-based shRNAs to block ERK1/2 and p38 activities in breast cancer cells as they previously described (Peng et al., 2005; Peng et al., 2005 and Ye et al., 2012). The optimal concentrations (10 µM) of different inhibitors used for these experiments, including SB203580 (p38 inhibitor) and U0126 (ERK1/2 inhibitor), were selected based on their toxic effects on tumor cell viability and proliferation. As shown in FIG. 5B, the inventors observed that inhibitors U0126 and SB203580 significantly reduced SALL1-induced senescent cell populations in both MCF-7 and E0771 breast tumor cells. They then used shRNA to specifically knock down p38 and ERK1/2 genes in MCF-7 and E0771 cells, and measured the effects on SALL1-induced tumor cell senescence (Peng et al., 2005 and Peng et al., 2007). Consistent with the results obtained in inhibitor experiments described above, knockdown of p38 and ERK1/2 in MCF-7 and E0771 cells significantly decreased the senescence induction in SALL1-transfected tumor cells (FIG. 5C). These results suggest that SALL1 expression in breast cancer cells induces selective modulation of specific MAPK p38 and ERK1/2 signaling pathways in tumor cells that control the molecular process of SALL1-induced tumor cell senescence and growth suppression. Moreover, this process depends on an intact NuRD-recruitment motif in SALL1.

In addition to MAPK signaling, increasing evidence suggests that mTOR kinase signaling activation is also important for tumor cell proliferation and senescence induction (Leontieva et al., 2010; Leontieva et al., 2011; Xu et al., 2014; Astle et al., 2012 and Kolesnichenko et al., 2012). The inventors next investigated whether mTOR signaling is also involved in the SALL1-induced breast cancer growth inhibition and senescence induction. The inventors determined the activation of mTOR and its downstream substrates p70S6K and 4E-BP1, in breast tumor cells after transfection with SALL1 (Weichhart et al., 2008). Transfection of SALL1 but not mutated SALL1 in both MCF-7 and E0771 breast tumor cells significantly induced the phosphorylation of mTOR, p70S6K, and 4E-BP1, further confirming the activation of mTOR signaling in tumor cells after SALL1 expression (FIG. 5D). Using the loss-of-function strategies, the inventors demonstrated that the mTOR inhibitor rapamycin and shRNA to specifically knock down mTOR genes in breast cancer cells dramatically prevented the senescence induction in tumor cells mediated by SALL1 expression (FIGS. 5E-F). These results suggest that the mTOR signaling pathway is also critical in regulating breast cancer cell senescence mediated by SALL1 expression. Furthermore, these studies indicate that SALL1 expression in breast cancer selectively utilizes both MAPK and mTOR signaling pathways controlling tumor cell fate and functions.

SALL1 Expression in Breast Cancer Cells Inhibits Tumorigenesis and Metastasis In Vivo.

Figure 6B:
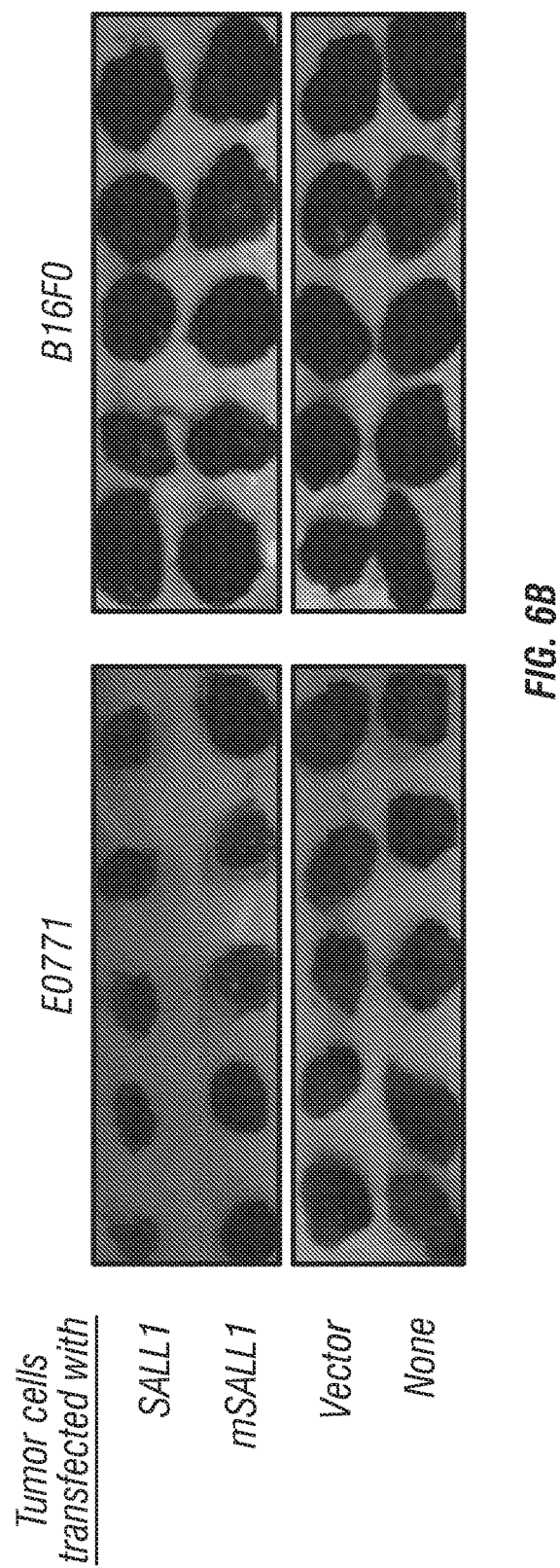
Figure 6C:
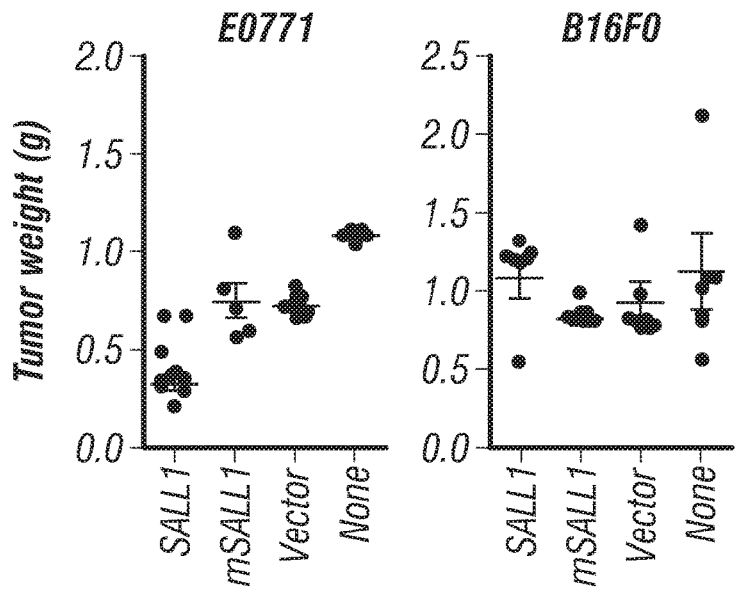
Figure 6D:
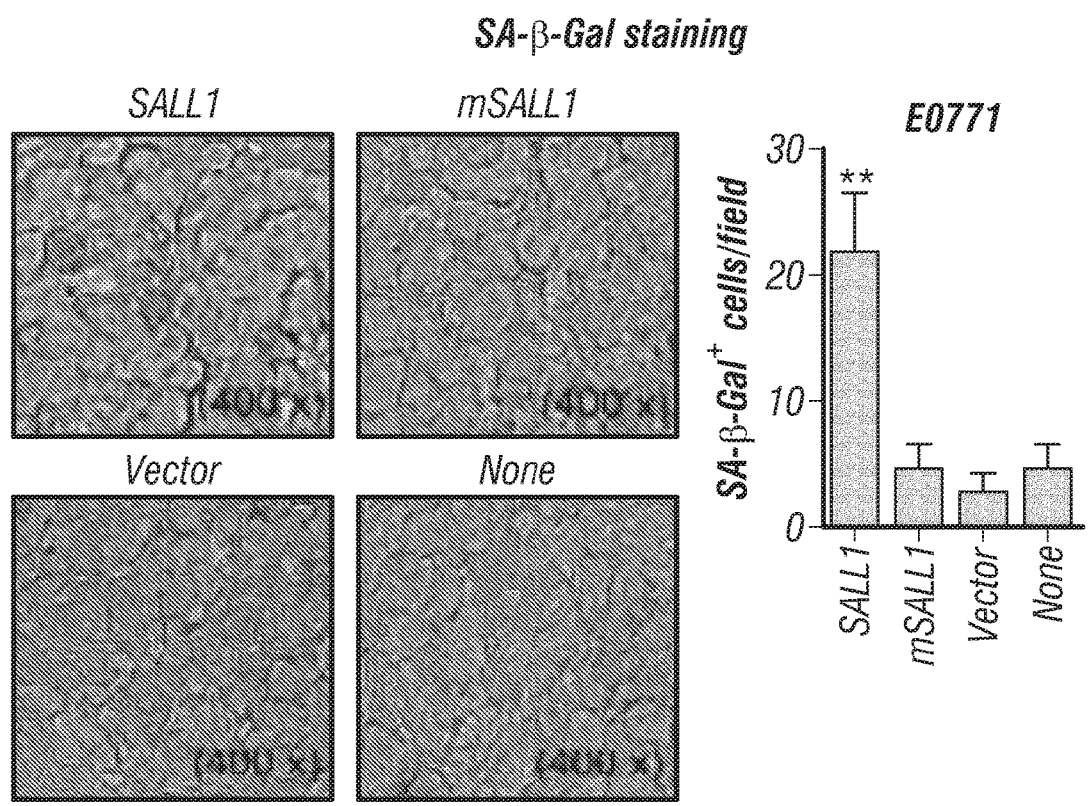

These in vitro studies provided us with important information regarding the mechanism and molecular signaling of SALL1 in suppressing breast cancer tumor cell growth and metastasis. The inventors next performed complementary in vivo studies, using murine breast cancer E0771 cells in humanized NOD-scid IL2Rgamma$^{null}$ (NSG) mouse models, and explored whether SALL1 functions as a tumor suppressor for the tumorigenesis and metastasis of breast cancer in vivo (Peng et al., 2005 and Peng et al., 2007). The E0771 cell line is derived from medullary breast adenocarcinoma cells, representing a good model for spontaneously developed breast cancer (Ewens et al., 2005). The inventors also included murine B16F0 melanoma cells as a tumor control for this study. They first performed xenograft models to investigate whether over-expression of SALL1 in breast cancer cells can affect tumor growth and development. Mouse E0771 and B16F0 tumor cells infected with Lentivirus carrying SALL1, mSALL1 or vector, were subcutaneously injected into NSG mice. Tumor growth was evaluated. At the end of the experiments, tumors were isolated from the sacrificed mice and weighed. As shown in FIG. 6A, the inventors observed that E0771 tumor cells alone or transfected with mutated SALL1 gene or vector control, grew progressively in NSG mice. However, over-expression of wild-type SALL1 in E0771 cells dramatically inhibited breast tumor progression and growth. Furthermore, tumor sizes collected from the E0771-SALL1 group on day 21 post inoculation were significantly smaller than those in the control groups of E0771 tumor alone, E0771 cells transfected with mSALL1 or vector (FIG. 6B). In addition, the average tumor weights obtained from the E0771-SALL1 group were much lower than those of the three control groups (FIG. 6C). Notably, tumor growth, tumor sizes and weights were very similar among the three control groups of E0771 tumor alone, E0771 cells transfected with mSALL1 or vector. In contrast to the E0771 breast tumor model, there were no differences of tumor growth, progression and sizes among the experimental groups of B16F0 cells transfected with SALL1, mSALL1 or vector, in the B16F0 melanoma model (FIGS. 6A-6C). These results were consistent with the in vitro studies showing that SALL1 had different effects and functions in breast and melanoma tumor cells. Furthermore, the inventors confirmed, using histochemical staining of SA-β-Gal expression on sections from embedded tumor tissues, that high amount of senescent tumor cells were observed in tumor tissues obtained from the E0771-SALL1 group, but not from the control groups of E0771 tumor alone, E0771 cells transfected with mSALL1 or vector (FIG. 6D). These results clearly suggest that SALL1 expression in breast tumor cells directly controls tumor growth and tumorigenesis.

Figure 7A:
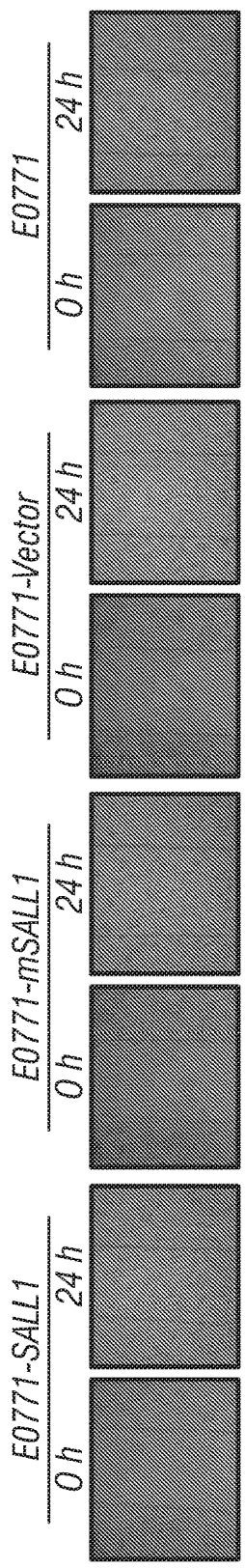
FIGS. 7A-E. SALL1 over-expression in breast cancer cells inhibited tumor metastasis in vivo.
Figure 7B:
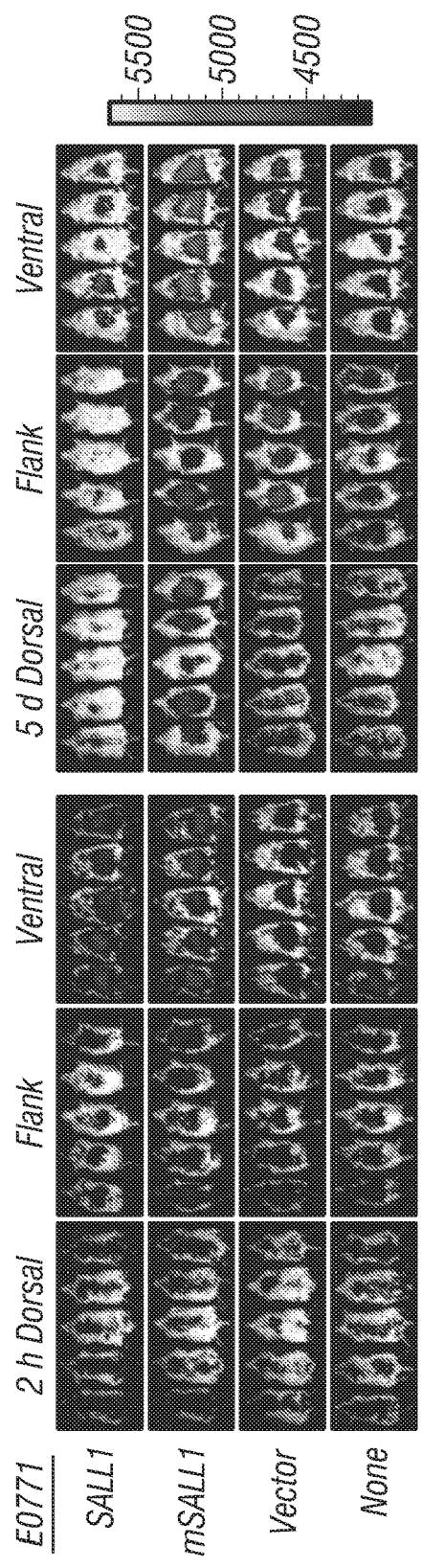
Figure 7C:
Figure 7E:
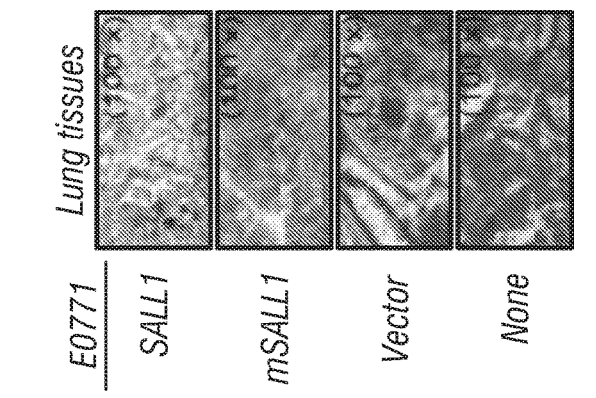
Figure 7D:
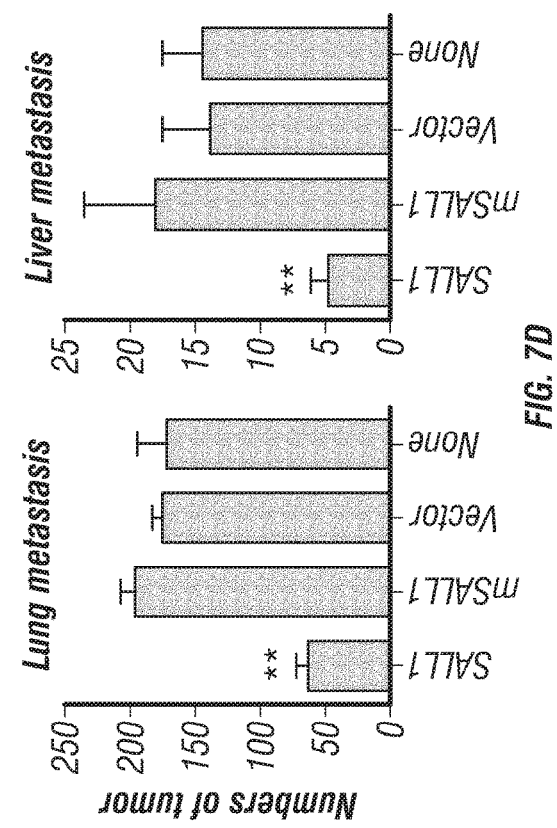
Figure 13A:
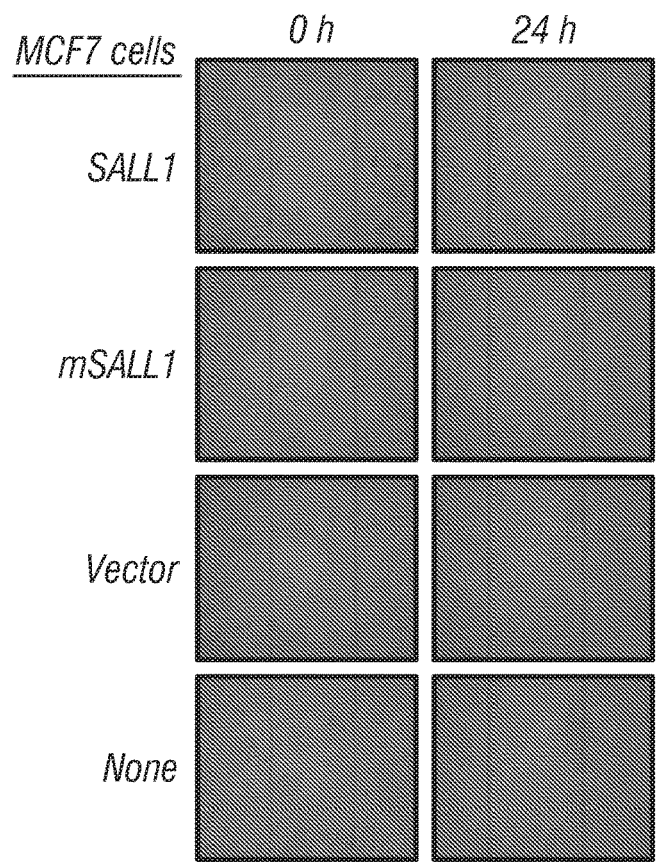
FIGS. 13A-C. SALL1 over-expression in breast cancer cells inhibited tumor metastasis in vivo.
Figure 13C:
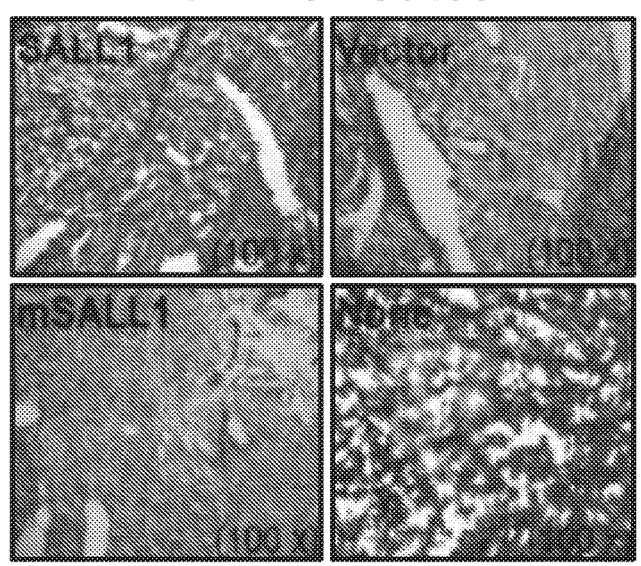
Figure 13B:
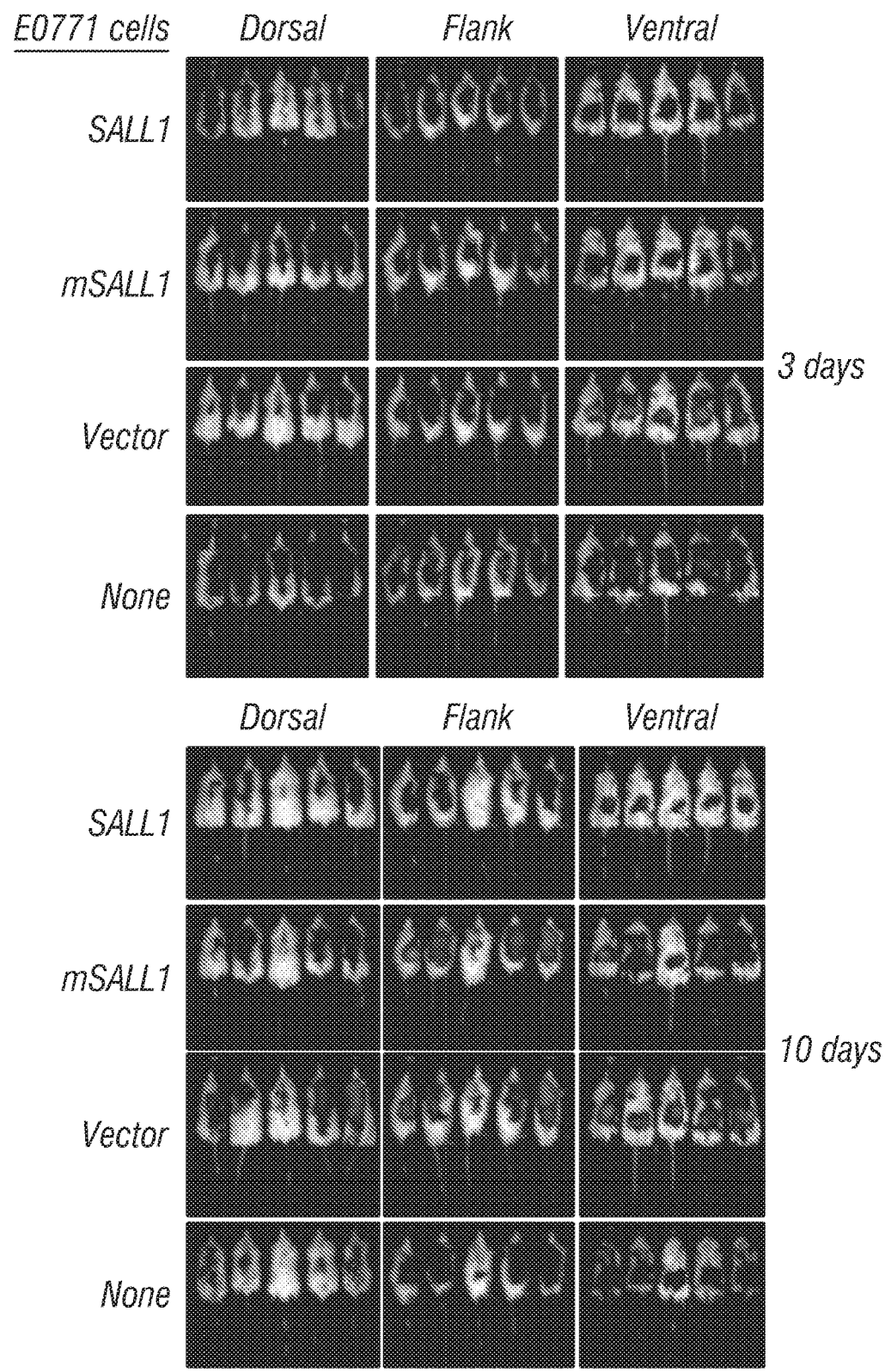

The inventors next investigated whether over-expression of the SALL1 gene inhibited breast tumor metastasis. In vitro wound closure assays were utilized to determine the capacity of tumor cell migration after transfection with or without SALL1 They observed that over-expression of SALL1 in E0771 and MCF7 breast tumor cells markedly inhibited the migration of tumor cells compared with the tumor cells alone, or tumor cells transfected with mSALL1 or vector (FIG. 7A and FIG. 13A). The inventors then investigated whether over-expression of SALL1 affected tumor metastasis using previously established adoptive transfer tumor models with a live imaging system (31, 32, 49). Mouse E0771 tumor cells infected with or without lentivirus carrying SALL1 or control mutated SALL1 gene were labeled with VivoTag®680 XL and then injected intravenously into the tail vein of NSG mice. Tumor cell distribution and metastasis in mice were imaged at dorsal, right lateral and ventral positions with an In Vivo Spectrum Imaging System (IVIS) at different time points post injection. As shown in FIG. 7B and FIG. 13B, at early time points (before 3 days) post tumor cell injection, tumor cells randomly migrated into different organs, including spleen, liver and lung with similar signal densities among different groups. The signal density of tumor cells significantly increased and accumulated in these sites in the late time points (after 3 days) post tumor cell transfer among the groups of E0771 tumor cells only, or transfected with mSALL1 or vector. This tumor cell accumulation with strong signal density continued to persist throughout the whole observation period (19 days), indicating accumulated metastasis of tumor cells into the lung and liver. However, the signal density from the tumor cells transfected with SALL1 group markedly decreased in the late time points (after 3 days) post tumor cell injection, suggesting the lower capacity of tumor metastasis and growth compared with that of the other groups. To further confirm the live imaging results, livers and lungs from the four groups were harvested at day 19 post tumor injection and macrometastatic tumors were evaluated. As expected, the inventors observed that transferred E0771 tumor cells alone or transfected with mutated SALL1 gene or vector control, significantly grew with metastasis in lungs and livers (FIGS. 7C-D). In contrast, transfection of SALL1 in E0771 cells dramatically decreased tumor macrometastatic numbers both in lung and in liver surfaces. Furthermore, they confirmed, using histological staining on sections from embedded liver and lung tissues that a high number of tumor cells infiltrated into livers and lungs obtained from control groups of mSALL1 and vector-transfected E0771, but not from the SALL1-transfected tumor group (FIG. 7E and FIG. 13C). These studies clearly demonstrate that SALL1 is a tumor suppressor in breast cancer and plays a critical role in directing tumorigenesis and metastasis.

Example 3—Discussion

SALL2 and SALL4 have been recently recognized as key regulators involving tumor tumorigenesis (Li, et al., 2001; Li, et al., 2004; Yang et al., 2008 and Li et al., 2013), but little information is known about the role of SALL1 gene in the regulation of tumor biology. In the current study, the inventors showed that SALL1 expression was significantly down-regulated in human breast cancer based on the clinical sample and cell line analyses. They further demonstrated that SALL1 expression in human and murine breast cancer cells suppressed tumor cell growth and proliferation in vitro, and inhibited tumorigenesis and metastasis in vivo in breast cancer models. Importantly, the tumor suppressor function mediated by SALL1 is mechanistically related to cell senescence induction via the recruitment of NuRD complex in cancer cells. These studies clearly indicate that SALL1 functions as a tumor suppressor in breast cancer, which could be a novel target for human breast cancer therapy.

One recent paper identified that SALL1 could be a tumor suppressor in human breast cancer, using an in vivo RNAi screen strategy (Wolf et al., 2014). They further demonstrated that high expression of SALL1 was associated with a significantly increased survival of breast cancer patients. However, whether and how SALL1 regulates human breast cancer is still unclear. Improved understanding of these molecular events should open new avenues for breast cancer clinical therapy. The inventors have extensively studied the molecular mechinasms responsible for SALL1-mediated regulation in kidney development, and demonstrated that endogenous SALL1 recruits and binds to the NuRD complex performing its transcriptional repression and regulation of specific developmental processes (Kiefer et al., 2010; Denner and Rauchman, 2013; Lauberth et al., 2007 and Lauberth & Rauchman, 2006). In this study, using both the loss-of-function (either deletion of the conserved NuRD-binding 12-amino acid peptide motif or substitution of the serine with a glutamic acid SALL1), and gain-of-function (mutating the serine to an alanine) strategies in vitro and in vivo studies, the inventors clearly demonstrated that SALL1 also utilizes a similar mechanism as in the developing kidney to recruit the NuRD complex, resulting in the inhibition of tumorigenesis and metastasis in breast cancer (Lauberth et al., 2007 and Lauberth & Rauchman, 2006). In support of these findings, studies from other groups have already shown that the key components of NuRD complex, including MTA1, MTA3, and Mi-2, and other NuRD interacting proteins such as LSD1, directly control the cancer invasive growth, epithelial-to-mesenchymal transition, and metastasis in breast cancer (Lai & Wade, 2011; Wang et al., 2009; Fujita et al., 2003 and Fu et al., 2011). The current studies further suggest a causative link between SALL1 gene regulation, NuRD complex involvement, and breast cancer pathogenesis. In addition to the recruitment of NuRD complex, SALL1 may also be involved in the regulation of other oncogenes, such as PTEN and c-Myc (11, 50). However, the inventors did not observe changes of these two oncogenes in breast cancer cells mediated by SALL1 overexpression (Data not shown). Notably, MTA1, MTA2 and MTA3 in NuRD complex have been shown to play an important role in ER and HER2 regulatory pathways regulating the epithelial-mesenchymal transition (EMT) and tumor cell invasion and matastasis, but they have different regulation patterns and effects (Lai & Wade, 2011; Fujita et al., 2003; Molli et al., 2008 and Mazumdar et al., 2001). Given that both ER and HER2 expression levels in tumor cells are important prognostic factors for breast cancer outcomes, the inventors also determined whether SALL1 had different expression in breast cancer patients with different ER, PR or HER2 expression statuses. The results suggested that SALL1 expression in HER2$^+$ patients was much higher than that in HER2$^-$ patients. In addition, SALL1$^+$ cell numbers in ER$^-$ patients were significant lower than those in ER$^+$ patients. Notbly, SALL1 expression showed a significant decrease in triple-negative breast cancer tissues. These results suggested that SALL1 tumor suppression may also involve hormone receptor and HER2 regulation in breast cancer. The inventors will continue their efforts to identify the molecular interactions and regulatory mechanisms between SALL1, NuRD and HER2, ER and PR, in the regulation of tumorigenesis and metastasis in breast cancer. In addition, given the multiple functions mediated by different subunits of the NuRD complex, identification of the precise assembly of NuRD components recruited by SALL1 in breast cancer cells will facilitate the understanding the functional role of SALL1 gene in tumor biology.

Besides the recruitment of NuRD complex, this study also identified senescence induction as a novel mechanism mediated by SALL1 for the regulation of tumor biology and tumorigenesis in human breast cancer. Cellular senescence was initially described more than 40 years ago in human fibroblasts with limited passages in cell culture. It is now well known that senescent cells have permanent cell cycle arrest, but remain viable, metabolically active and possess unique transcriptional profiles and gene regulation signatures. There are two major categories of cellular senescence: (1) Replicative senescence (telomere-dependent senescence) occurs due to telomere shortening or dysfunction that triggers a classical DNA-damage response (d'Adda di Fagagna et al., 2003 and Herbig et al., 2004); and (2) Premature senescence (extrinsic senescence or telomere-independent senescence) is induced by a variety of extrinsic forms of stress, such as oxidative stress, DNA damage, and activation of certain oncogenes, as well as some inflammatory cytokines and chemokines (Lleonart et al., 2009). The inventors have recently demonstrated that human Treg cells can also induce responder T cell senescence (Ye et al., 2013 and Ye et al., 2012). In addition, cellular senescence is now thought to be a tumor suppressive mechanism and senescence induction could be a possible cancer therapy strategy (Lleonart et al., 2009 and Campisi, 2013). In this study, the inventors were the first to show that SALL1 also plays critical role in control of genome stability, cell-cycle progression and cell fate in breast cancer. Specifically, they observed that SALL1 gene expression in breast cancer strongly suppresses tumor growth and proliferation, as well as induces cell cycle S phase arrest, which is mechanistically independent of apoptosis or cytolysis. They further discovered that SALL1-mediated suppression of breast cancer cells is due to the induction of tumor cell senescence evidencing by induction of SA-β-Gal (Ye et al., 2013 and Ye et al., 2012). In addition, they identified that ATM-associated DNA damage is responsible for SALL1-mediated breast cancer cell senescence, analyzing ATM and related molecule expression and activation, as well as using the loss-of-function approach with specific pharmacological ATM inhibitor. Importantly, the inventors also provide evidence demonstrating that the SALL1-mediated suppression of tumor growth and proliferation and induction of tumor cell senescence depends on the endogenous recruitment of NuRD complex in breast cancer cells. The regulation of cell cycle transition and DNA damage responses mediated by the NuRD complex has been well recognized (25). MTA1 and MTA2 can directly regulate p53 stability and function, leading to growth arrest inhibition and DNA damage response regulation (Li et al., 2009 and Li et al., 2009). The chromodomain helicase DNA-binding protein 4 (CHD4) is also as an important regulator of the G1/S cell cycle transition and ATM-associated DNA damage responses (Polo et al., 2010 and Polo et al., 2010). In addition, HDAC1 and HDAC2 regulate the DNA-damage response and cellular senescence (Miller et al., 2010 and Willis-Martinez et al., 2010). Future studies will continue to focus on the identification of the subunits of NuRD recruited by SALL1 in breast cancer cells responsible for the regulation of DNA-damage response and senescence induction. Interestingly, one study suggested that SALL2 gene directly binds to p21 promoter promoting cell cycle arrest and inhibiting cell growth (Li, et al., 2004). Therefore, whether SALL1 can also directly regulate cell cycle regulator molecules is another potential mechanism that needs to be explored.

Dissection of the unique molecular signaling responsible for SALL1-mediated tumor suppression is another challenge. These studies clearly showed that SALL1 expression in breast tumor cells selectively modulated the specific MAPK p38 and ERK1/2, as well as mTOR signaling pathways in tumor cells. In addition, the loss-of-function studies with specific pharmacological inhibitors and lentivirus-based shRNAs further indicated that SALL1-mediated tumor suppression and senescence induction is controlled by both MAPK and mTOR signaling pathways. It is well recognized that MAPK signaling pathways play a major role in regulating cell cycle re-entry, oncogenic ras-induced senescence and G1 cell cycle arrest (Wang et al., 2002; Kwong et al., 2009 and Todd et al., 2004). The inventors' recent studies further demonstrated that MAPK ERK1/2 and p38 signaling controls the molecular process of human CD4$^+$ CD25$^{hi}$FoxP3$^+$ Treg-induced responder T cell senescence (Ye et al., 2012). In addition to MAPK signaling, mTOR kinase signaling activation is important for tumor cell proliferation and senescence induction (Leontieva et al., 2010). mTOR signaling is also involved in the oncogene-induced DNA damage responses and cell senescence (Xu et al., 2014; Astle et al., 2012 and Weichhart et al., 2008). The current studies further identified the important roles of these two signaling pathways in SALL1-mediated regulation in breast cancer cells. However, the results presented here are different from the inventors' previous observations showing that SALL1 induces Wnt signaling in the developing kidney (Kiefer et al., 2010 and Kiefer et al., 2010). Interestingly, the inventors did not find the activation of Wnt signaling in breast cancer MCF-7 and E0771 cells induced by SALL1 over-expression. These results suggest that the molecular signaling utilized by SALL1 promoting its tumor suppressor function is different from that in the regulation of organ development. Further dissection of how MAPK signaling and mTOR signaling cooperate and identification of unique adaptor molecules controlling SALL1 biological functions in tumor cells will be critical preludes for the application of SALL1 and tumor senescence as new targets for tumor therapeutic interventions.

In summary, the inventors identified SALL1 as a tumor suppressor in breast cancer and demonstrated that SALL1 induced tumor cell senescence as a novel mechanism of tumor suppressor function. This molecular process is through NuRD recruitment and controlled by MAPK and mTOR signaling pathways. These studies not only reveal a novel role of SALL1 in breast cancer biology, but also provide the mechanistic and causative links among SALL1 regulation, cellular senescence, NuRD involvement, as well as MAPK and mTOR signaling pathways. These important aspects should also provide new insights relevant for the development of novel therapeutic strategies in human breast cancer and other cancers as well.

All of the compositions and methods disclosed and claimed herein can be made and executed without undue experimentation in light of the present disclosure. While the compositions and methods of this disclosure have been described in terms of particular embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference:

U.S. Pat. No. 4,554,101
U.S. Pat. No. 4,683,195
U.S. Pat. No. 4,683,202
U.S. Pat. No. 4,684,611
U.S. Pat. No. 4,879,236
U.S. Pat. No. 4,952,500
U.S. Pat. No. 5,217,879
U.S. Pat. No. 5,302,523
U.S. Pat. No. 5,322,783
U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
EPO 0273085
Al-Baradie et al., *Am J Hum Genet* 71: 1195-9, 2002.
Almendro et al., *J. Immunol.*, 157(12):5411-5421, 1996.
Amado and Chen, *Science*, 285(5428):674-676, 1999.
Armentano et al., *Proc. Natl. Acad. Sci. USA*, 87(16):6141-6145, 1990.
Astle et al., *Oncogene* 31: 1949-62, 2012.
Ausubel et al., In: *Current Protocols in Molecular Biology*, John, Wiley & Sons, Inc, New York, 1994.
Batra et al., *Am. J Respir. Cell Mol. Biol.*, 21(2):238-245, 1999.
Bellus, *J Macromol. Sci. Pure Appl. Chem.*, A31(1): 1355-1376, 1994.
Bett et al., *J Virololgy*, 67(10):5911-5921, 1993.
Bilbao et al., *Transplant Proc.*, 31(1-2):792-793, 1999.
Blackwell et al., *Arch. Otolaryngol. Head. Neck Surg.*, 125(8):856-863, 1999.
Blomer et al., *J Virol.*, 71(9):6641-6649, 1997.
Borozdin et al., *J Med Genet* 41: e113, 2004.
Campisi, *Annu Rev Physiol* 75: 685-705, 2013.
Cao et al., *Cancer* 115: 2640-51, 2009.
Capaldi et al., *Biochem. Biophys. Res. Comm.*, 76:425, 1977.
Caplen et al., *Gene Ther.*, 6(3):454-459, 1999.
Case et al., *Proc. Natl. Acad. Sci. USA*, 96(6):2988-2893, 1999.
Chandler et al., *Proc. Natl. Acad. Sci. USA*, 94(8):3596-601, 1997.
Chen and Okayama, *Mol. Cell. Biol.* 7:2745-2752, 1987.
Chen et al., *Genes Dev.*, 10:2438-2451, 1996.
Chillon et al., *J. Virol.*, 73(3):2537-2540, 1999.
Clay et al., *Pathol. Oncol. Res.*, 5(1):3-15, 1999.
Coffey et al., *Science*, 282(5392):1332-1334, 1999.
Culver et al., *Science*, 256(5063):1550-1552, 1992.
d'Adda di Fagagna et al., *Nature* 426: 194-8, 2003.
DeLuca et al., *J Virol.*, 56(2):558-570, 1985.
Derby et al., *Hear Res.*, 134(1-2):1-8, 1999.
Dorai et al., *Int. J Cancer*, 82(6):846-852, 1999.
Engel and Kohn, *Front Biosci.*, 4:e26-33, 1999.
Ewens et al., *Anticancer Res* 25: 3905-15, 2005.
Fechheimer, et al., *Proc Natl. Acad. Sci. USA*, 84:8463-8467, 1987.
Feldman et al., *Semin. Interv. Cardiol.*, 1(3):203-208, 1996.
Feng et al., *Nat. Biotechnol.*, 15(9):866-870, 1997.
Fisher et al., *Virology*, 217(1):11-22, 1996.

Fraley et al., *Proc. Natl. Acad. Sci. USA*, 76:3348-3352, 1979.
Fu et al., *Cell Res* 21: 275-89, 2011.
Fujita et al., *Cell* 113: 207-19, 2003.
Fujiwara and Tanaka, *Nippon Geka Gakkai Zasshi*, 99(7):463-468, 1998.
Garoff and Li, *Curr. Opin. Biotechnol.*, 9(5):464-469, 1998.
Garrido et al., *J. Neurovirol.*, 5(3):280-288, 1999.
Ghosh and Bachhawat, *In: Liver Diseases, Targeted Diagnosis and Therapy Using Specific Receptors and Ligands*, Wu and Wu (Eds.), Marcel Dekker, New York, 87-104, 1991.
Gnant et al., *Cancer Res.*, 59(14):3396-403, 1999.
Gnant et al., *J Natl. Cancer Inst.*, 91(20):1744-1750, 1999.
Gnemmi et al., *Histopathology* 63: 425-8, 2013.
Gopal, *Mol. Cell. Biol.*, 5:1188-1190, 1985.
Graham and Prevec, *Mol. Biotechnol.*, 3(3):207-220, 1995.
Graham and Van Der Eb, *Virology* 52:456-467, 1973
Guo et al., *EMBO J* 26: 4709-19, 2007.
Haecker et al., *Hum. Gene Ther.*, 7(15):1907-1914, 1996.
Han et al., *Euro. J Surgical Oncology*, 25:194-198, 1999.
Harland and Weintraub, *J. Cell Biol.*, 101:1094-1099, 1985.
Hayashi et al., *Neurosci. Lett.*, 267(1):37-40, 1999.
Herbig et al., *Mol Cell* 14: 501-13, 2004.
Hermens and Verhaagen, *Prog. Neurobiol.*, 55(4):399-432, 1998.
Hill et al., *Mol Cancer* 9: 51, 2010.
Holzer et al., *Virology*, 253(1):107-114, 1999.
Howard et al., *Ann. NY Acad Sci.*, 880:352-365, 1999.
Huard et al., *Neuromuscul Disord.*, 7(5):299-313, 1997.
Imai et al., *J Virol.*, 72(5):4371-4378, 1998.
Irie et al., *Antisense Nucleic Acid Drug Dev.*, 9(4):341-349, 1999.
Johnson et al., *IN: Biotechnology And Pharmacy*, Pezzuto et al., (Eds.), Chapman and Hall, New York, 1993.
Johnston et al., *J Virol.*, 73(6):4991-5000, 1999.
Kaeppler et al., *Plant Cell Reports*, 9:415-418, 1990.
Kaneda et al., *Science*, 243:375-378, 1989.
Kato et al., *J. Biol. Chem.*, 266(6):3361-3364, 1991.
Kaufman et al., *Surv. Ophthalmol.*, 43 Suppl 1:S91-97, 1999.
Kay, *Haemophilia*, 4(4):389-392, 1998.
Kiefer et al., *Development* 137: 3099-12010.
Kiefer et al., *Hum Mutat* 29: 1133-40, 2008.
Kiefer et al., *J Biol Chem* 277: 14869-76, 2002
Klimatcheva et al., *Front Biosci.* 4:D481-96, 1999.
Kohlhase et al., *Genomics* 62: 216-22, 1999.
Kohlhasew et al., *Genomics* 38: 291-8, 1996.
Kohut et al., *Am. J Physiol.*, 275(6 Pt 1):L1089-94, 1998.
Kolesnichenko et al., *Cell Cycle* 11: 2391-401, 2012.
Kooby et al., *FASEB J*, 13(11):1325-1334, 1999.
Kraus et al., *FEBS Lett.*, 428(3):165-170, 1998.
Krisky et al., *Gene The.r*, 5(11):1517-1530, 1998a Krisky et al., *Gene Ther.*, 5(12):1593-1603, 1998b.
Kwong et al., *J Biol Chem* 284: 11237-46, 2009.
Lachmann and Efstathiou, *Clin. Sci. (Colch)*, 96(6):533-541, 1999.
Lai & Wade, *Nat Rev Cancer* 11: 588-96, 2011.
Lareyre et al., *J Biol. Chem.*, 274(12):8282-8290, 1999.
Laspia et al., *Cell*, 59:283, 1989.
Latimer et al., *Mol. Cell. Biol.*, 10:760, 1990.
Lauberth et al., *J Biol Chem* 281: 23922-31, 2006.
Lauberth et al., *J Biol Chem* 282: 34858-68, 2007.
Leibowitz et al., *Diabetes*, 48(4):745-753, 1999.
Leontieva et al., *Aging* (Albany N.Y.) 2: 924-35, 2010.
Leontieva et al., *PLoS One* 6: e26126, 2011.
Lesch, *Biol. Psychiatry*, 45(3):247-253, 1999.
Li et al., *J Biol Chem* 284: 34545-52, 2009.
Li et al., *Proc Natl Acad Sci USA* 106: 17493-8, 2009.
Li et al., *J Clin Invest* 123: 4195-207, 2013.
Lin et al., *Mol. Cell. Biol.*, 10:850, 1990.
Lleonart et al., *Mol Cancer* 8:3, 2009.
Love et al., *Nat Genet* 44: 1321-5, 2012.
Lu et al., *PLoS One* 4: e5577, 2009.
Lundstrom, *J. Recept. Signal Transduct. Res.*, 19(1-4):673-686, 1999.
Ma et al., *J Biol Chem* 276: 48223-30, 2001.
Ma et al., *J Immunol* 189: 5029-36, 2012.
Marienfeld et al., *Gene Ther.*, 6(6):1101-1113, 1999.
Mastrangelo et al., *Cancer Gene Ther.*, 6(5):409-422 1999.
Mazumdar et al., *Nat Cell Biol* 3: 30-7, 2001.
Miller et al., *Methods Enzymol.*, 217:581-599, 1993.
Miller et al., *Nat Struct Mol Biol* 17: 1144-51, 2010.
Miyatake et al., *Gene Ther.*, 6(4):564-572, 1999.
Moldawer et al., *Shock*, 12(2):83-101, 1999.
Molli et al., *Oncogene* 27: 1971-80, 2008.
Moriuchi et al., *Cancer Res.*, 58(24):5731-5737, 1998.
Morrison et al., *J Gen. Virol.*, 78(Pt 4):873-878, 1997.
Naldini et al., *Proc. Natl. Acad. Sci. USA*, 93(21):11382-11388, 1996.
Nicolau and Sene, *Biochim. Biophys. Acta*, 721:185-190, 1982.
Nicolau et al., *Methods Enzymol.*, 149:157-176, 1987
Nomoto et al., *Gene*, 236(2):259-271, 1999.
Omirulleh et al., *Plant Mol. Biol.*, 21(3):415-28, 1993.
Osafune et al., *Development* 133: 151-61, 2006.
Parks et al., *J. Virol.*, 71(4):3293-8, 1997.
Perales et al., *Proc. Natl. Acad. Sci. USA*, 91:4086-4090, 1994.
Petrof, *Eur. Respir. J.*, 11(2):492-497, 1998.
Polo et al., *EMBO J* 29: 3130-9 2010.
Potrykus et al., *Mol. Gen. Genet.*, 199:183-188, 1985.
Potter et al., *Proc. Natl. Acad. Sci. USA*, 81:7161-7165, 1984.
Rabinovitch et al., *Diabetes*, 48(6):1223-1229, 1999.
Reddy et al., *J Virol.*, 72(2):1394-1402, 1998.
Remington's Pharmaceutical Sciences, 15$^{th}$ ed., pages 1035-1038 and 1570-1580, Mack Publishing Company, Easton, Pa., 1980.
*Remington's Pharmaceutical Sciences* 15th Edition, 33:624-652, 1990
Rippe et al., "DNA-mediated gene transfer into adult rat hepatocytes in primary culture," *Mol. Cell Biol.*, 10:689-695, 1990.
Robbins and Ghivizzani, *Pharmacol. Ther.*, 80(1):35-47, 1998.
Robbins et al., *Proc. Natl. Acad. Sci. USA*, 95(17):10182-10187 1998.
Robbins et al., *Trends Biotechnol.*, 16(1):35-40, 1998.
Rodier et al., *Nat Cell Biol* 11: 973-9, 2009.
Sambrook et al., *In: Molecular Cloning: A Laboratory Manual*, Vol. 1, Cold Spring Harbor Laboratory Press, Cold Spring Harbor, N.Y., Ch. 7, 7.19-17.29, 1989.
Sato et al., *Biochem Biophys Res Commun* 319: 103-13, 2004.
Sawai et al., *Mol. Genet. Metab.*, 67(1):36-42, 1999.
Smith, *Arch. Neurol.*, 55(8):1061-1064, 1998.
Stewart et al., *Gene Ther.*, 6(3):350-363, 1999.
Suzuki et al., *Biochem. Biophys. Res. Commun.*, 252(3):686-690, 1998.
Tanaka et al., *Oncogene*, 8:2253-2258, 1993.
Timiryasova et al., *Int. J Oncol.*, 14(5):845-854, 1999.
Timiryasova et al., *Oncol. Res.*, 11(3):133-144, 1999.
Todd et al., *Oncogene* 23: 3284-95, 2004.

Tsumaki et al., *J. Biol. Chem.*, 273(36):22861-22864, 1998.
Tur-Kaspa et al., *Mol. Cell Biol.*, 6:716-718, 1986.
Ushiku et al., *Am J Surg Pathol* 34: 533-40, 2010.
Vanderkwaak et al., *Gynecol. Oncol.*, 74(2):227-234, 1999.
Wagner et al., *Science*, 260:1510-1513, 1990.
Wang et al., *Cell* 138: 660-72, 2009.
Wang et al., *Gynecol. Oncol.*, 71(2):278-287, 1998.
Wang et al., *Mol Cell Biol* 22: 3389-403, 2002
Weichhart et al., *Immunity* 29: 565-77, 2008.
Weihl et al., *Neurosurgery*, 44(2):239-252, 1999.
White et al., *J. Virol.*, 73(4):2832-28340, 1999.
Willis-Martinez et al., *Exp Gerontol* 45: 279-85, 2010.
Wilson, *J. Clin. Invest.*, 98(11):2435, 1996.
Wolf et al., *Oncogene* 33: 4273-8, 2014.
Wong et al., *Gene*, 10:87-94, 1980.
Wu and Wu, *J Biol. Chem.*, 262:4429-4432, 1987.
Wu et al., *Biochem. Biophys. Res. Commun.*, 233(1):221-226, 1997.
Wu, *Chung Hua Min Kuo Hsiao Erh Ko I Hsueh Hui Tsa Chih*, 39(5):297-300, 1998.
Xu et al., *Trends Biochem Sci* 39: 268-76, 2014.
Yamada et al., *Proc. Natl. Acad. Sci. USA*, 96(7):4078-4083, 1999.
Yang and Liang, *Mol Biotechnol.*, 3:197-208, 2004.
Yang et al., *Blood* 112: 805-13, 2008.
Yang et al., *Proc Natl Acad Sci USA* 105: 19756-61, 2008.
Ye et al., *Blood* 120: 2021-31, 2012.
Ye et al., *Cancer Res* 73: 6137-48, 2013.
Ye et al., *J Immunol* 190: 2403-14, 2013.
Yeung et al., *Gene Ther.*, 6(9):1536-1544, 1999.
Yoon et al., *J Gastrointest. Surg.*, 3(1):34-48, 1999.
Zhao-Emonet et al., *Biochim. Biophys. Acta*, 1442(2-3):109-119, 1998.
Zheng et al., *J Gen. Virol.*, 80(Pt 7):1735-1742, 1999.
Zufferey et al., *Nat. Biotechnol.*, 15(9):871-875, 1997.

What is claimed is:

1. A method for suppressing the growth, proliferation, migration and metastasis of a breast cancer cell or a prostate cancer cell comprising contacting said cell with an expression cassette comprising a polynucleotide encoding SALL1, wherein said polynucleotide is under the control of a promoter operable in eukaryotic cells, wherein expression of a SALL1 polypeptide results in suppression of the growth, proliferation, migration and metastasis of said cancer cell.

2. The method of claim 1, wherein said promoter is heterologous to the polynucleotide sequence.

3. The method of claim 2, wherein said promoter is selected from the group consisting of hsp68, SV40, CMV, MKC, $GAL4_{UAS}$, HSV and β-actin.

4. The method of claim 1, wherein said promoter is a tissue specific promoter.

5. The method of claim 1, wherein said promoter is an inducible promoter.

6. The method of claim 1, wherein said expression cassette is contained in a replication-competent expression vector.

7. The method of claim 6, wherein said replication-competent expression vector is a viral vector.

8. The method of claim 7, wherein said viral vector is selected from the group consisting of a retroviral vector, an adenoviral vector, and adeno-associated viral vector, a vaccinia viral vector, and a herpesviral vector.

9. The method of claim 6, wherein said replication-competent expression vector is a non-viral vector.

10. The method of claim 9, wherein said non-viral vector is encapsulated in a lipid delivery vehicle or a nanoparticle.

11. The method of claim 1, wherein said expression cassette further comprises a polyadenylation signal.

12. The method of claim 1, further comprising contacting said cancer cell with a second anti-cancer therapy.

13. The method of claim 1, wherein said cancer cell is a breast cancer cell.

14. The method of claim 1, wherein said cancer cell is located in a human subject.

15. The method of claim 14, wherein said expression cassette is administered systemically.

16. The method of claim 14, wherein said expression cassette is administered local or regional to a tumor site.

17. The method of claim 16, wherein said expression cassette is administered by intra-tumoral injection or to a resected tumor bed.

18. The method of claim 14, further comprising assessing SALL1 structure, expression and/or function in a sample from said subject.

19. The method of claim 1, wherein said cancer cell is a prostate cancer cell.

* * * * *

SEQUENCE LISTING

<160> NUMBER OF SEQ ID NOS: 10

<210> SEQ ID NO 1
<211> LENGTH: 1324
<212> TYPE: PRT
<213> ORGANISM: Homo sapiens

<400> SEQUENCE: 1

```
Met Ser Arg Arg Lys Gln Ala Lys Pro Gln His Phe Gln Ser Asp Pro
1               5                   10                  15

Glu Val Ala Ser Leu Pro Arg Arg Asp Gly Asp Thr Glu Lys Gly Gln
                20                  25                  30

Pro Ser Arg Pro Thr Lys Ser Lys Asp Ala His Val Cys Gly Arg Cys
            35                  40                  45

Cys Ala Glu Phe Phe Glu Leu Ser Asp Leu Leu Leu His Lys Lys Asn
        50                  55                  60

Cys Thr Lys Asn Gln Leu Val Leu Ile Val Asn Glu Asn Pro Ala Ser
65                  70                  75                  80

Pro Pro Glu Thr Phe Ser Pro Ser Pro Pro Asp Asn Pro Asp Glu
                85                  90                  95

Gln Met Asn Asp Thr Val Asn Lys Thr Asp Gln Val Asp Cys Ser Asp
                100                 105                 110

Leu Ser Glu His Asn Gly Leu Asp Arg Glu Glu Ser Met Glu Val Glu
            115                 120                 125

Ala Pro Val Ala Asn Lys Ser Gly Ser Gly Thr Ser Ser Gly Ser His
        130                 135                 140

Ser Ser Thr Ala Pro Ser Ser Ser Ser Ser Ser Ser Ser Ser Ser Gly
145                 150                 155                 160

Gly Gly Gly Ser Ser Ser Thr Gly Thr Ser Ala Ile Thr Thr Ser Leu
                165                 170                 175

Pro Gln Leu Gly Asp Leu Thr Thr Leu Gly Asn Phe Ser Val Ile Asn
            180                 185                 190

Ser Asn Val Ile Ile Glu Asn Leu Gln Ser Thr Lys Val Ala Val Ala
        195                 200                 205

Gln Phe Ser Gln Glu Ala Arg Cys Gly Gly Ala Ser Gly Gly Lys Leu
    210                 215                 220

Ala Val Pro Ala Leu Met Glu Gln Leu Leu Ala Leu Gln Gln Gln Gln
225                 230                 235                 240

Ile His Gln Leu Gln Leu Ile Glu Gln Ile Arg His Gln Ile Leu Leu
```

```
                        245                 250                 255
Leu Ala Ser Gln Asn Ala Asp Leu Pro Thr Ser Ser Pro Ser Gln
            260                 265                 270

Gly Thr Leu Arg Thr Ser Ala Asn Pro Leu Ser Thr Leu Ser Ser His
            275                 280                 285

Leu Ser Gln Gln Leu Ala Ala Ala Gly Leu Ala Gln Ser Leu Ala
290                 295                 300

Ser Gln Ser Ala Ser Ile Ser Gly Val Lys Gln Leu Pro Pro Ile Gln
305                 310                 315                 320

Leu Pro Gln Ser Ser Gly Asn Thr Ile Ile Pro Ser Asn Ser Gly
            325                 330                 335

Ser Ser Pro Asn Met Asn Ile Leu Ala Ala Val Thr Thr Pro Ser
            340                 345                 350

Ser Glu Lys Val Ala Ser Ala Gly Ala Ser His Val Ser Asn Pro
            355                 360                 365

Ala Val Ser Ser Ser Ser Pro Ala Phe Ala Ile Ser Ser Leu Leu
            370                 375                 380

Ser Pro Ala Ser Asn Pro Leu Leu Pro Gln Gln Ala Ser Ala Asn Ser
385                 390                 395                 400

Val Phe Pro Ser Pro Leu Pro Asn Ile Gly Thr Thr Ala Glu Asp Leu
                    405                 410                 415

Asn Ser Leu Ser Ala Leu Ala Gln Gln Arg Lys Ser Lys Pro Pro Asn
                420                 425                 430

Val Thr Ala Phe Glu Ala Lys Ser Thr Ser Asp Glu Ala Phe Phe Lys
            435                 440                 445

His Lys Cys Arg Phe Cys Ala Lys Val Phe Gly Ser Asp Ser Ala Leu
            450                 455                 460

Gln Ile His Leu Arg Ser His Thr Gly Glu Arg Pro Phe Lys Cys Asn
465                 470                 475                 480

Ile Cys Gly Asn Arg Phe Ser Thr Lys Gly Asn Leu Lys Val His Phe
                    485                 490                 495

Gln Arg His Lys Glu Lys Tyr Pro His Ile Gln Met Asn Pro Tyr Pro
                500                 505                 510

Val Pro Glu His Leu Asp Asn Ile Pro Thr Ser Thr Gly Ile Pro Tyr
            515                 520                 525

Gly Met Ser Ile Pro Pro Glu Lys Pro Val Thr Ser Trp Leu Asp Thr
            530                 535                 540

Lys Pro Val Leu Pro Thr Leu Thr Thr Ser Val Gly Leu Pro Leu Pro
545                 550                 555                 560

Pro Thr Leu Pro Ser Leu Ile Pro Phe Ile Lys Thr Glu Glu Pro Ala
                    565                 570                 575

Pro Ile Pro Ile Ser His Ser Ala Thr Ser Pro Pro Gly Ser Val Lys
                580                 585                 590

Ser Asp Ser Gly Gly Pro Glu Ser Ala Thr Arg Asn Leu Gly Gly Leu
            595                 600                 605

Pro Glu Glu Ala Glu Gly Ser Thr Leu Pro Pro Ser Gly Gly Lys Ser
            610                 615                 620

Glu Glu Ser Gly Met Val Thr Asn Ser Val Pro Thr Ala Ser Ser Ser
625                 630                 635                 640

Val Leu Ser Ser Pro Ala Ala Asp Cys Gly Pro Ala Gly Ser Ala Thr
                    645                 650                 655

Thr Phe Thr Asn Pro Leu Leu Pro Leu Met Ser Glu Gln Phe Lys Ala
                    660                 665                 670
```

```
Lys Phe Pro Phe Gly Gly Leu Leu Asp Ser Ala Gln Ala Ser Glu Thr
            675                 680                 685

Ser Lys Leu Gln Gln Leu Val Glu Asn Ile Asp Lys Lys Ala Thr Asp
        690                 695                 700

Pro Asn Glu Cys Ile Ile Cys His Arg Val Leu Ser Cys Gln Ser Ala
705                 710                 715                 720

Leu Lys Met His Tyr Arg Thr His Thr Gly Glu Arg Pro Phe Lys Cys
                725                 730                 735

Lys Ile Cys Gly Arg Ala Phe Thr Thr Lys Gly Asn Leu Lys Thr His
            740                 745                 750

Tyr Ser Val His Arg Ala Met Pro Pro Leu Arg Val Gln His Ser Cys
        755                 760                 765

Pro Ile Cys Gln Lys Lys Phe Thr Asn Ala Val Val Leu Gln Gln His
770                 775                 780

Ile Arg Met His Met Gly Gly Gln Ile Pro Asn Thr Pro Val Pro Asp
785                 790                 795                 800

Ser Tyr Ser Glu Ser Met Glu Ser Asp Thr Gly Ser Phe Asp Glu Lys
                805                 810                 815

Asn Phe Asp Asp Leu Asp Asn Phe Ser Asp Glu Asn Met Glu Asp Cys
            820                 825                 830

Pro Glu Gly Ser Ile Pro Asp Thr Pro Lys Ser Ala Asp Ala Ser Gln
        835                 840                 845

Asp Ser Leu Ser Ser Ser Pro Leu Pro Leu Glu Met Ser Ser Ile Ala
850                 855                 860

Ala Leu Glu Asn Gln Met Lys Met Ile Asn Ala Gly Leu Ala Glu Gln
865                 870                 875                 880

Leu Gln Ala Ser Leu Lys Ser Val Glu Asn Gly Ser Ile Glu Gly Asp
                885                 890                 895

Val Leu Thr Asn Asp Ser Ser Val Gly Gly Asp Met Glu Ser Gln
            900                 905                 910

Ser Ala Gly Ser Pro Ala Ile Ser Glu Ser Thr Ser Ser Met Gln Ala
        915                 920                 925

Leu Ser Pro Ser Asn Ser Thr Gln Glu Phe His Lys Ser Pro Ser Ile
930                 935                 940

Glu Glu Lys Pro Gln Arg Ala Val Pro Ser Glu Phe Ala Asn Gly Leu
945                 950                 955                 960

Ser Pro Thr Pro Val Asn Gly Gly Ala Leu Asp Leu Thr Ser Ser His
                965                 970                 975

Ala Glu Lys Ile Ile Lys Glu Asp Ser Leu Gly Ile Leu Phe Pro Phe
            980                 985                 990

Arg Asp Arg Gly Lys Phe Lys Asn  Thr Ala Cys Asp Ile  Cys Gly Lys
        995                 1000                1005

Thr Phe  Ala Cys Gln Ser Ala  Leu Asp Ile His Tyr  Arg Ser His
        1010                1015                1020

Thr Lys  Glu Arg Pro Phe Ile  Cys Thr Val Cys Asn  Arg Gly Phe
        1025                1030                1035

Ser Thr  Lys Gly Asn Leu Lys  Gln His Met Leu Thr  His Gln Met
        1040                1045                1050

Arg Asp  Leu Pro Ser Gln Leu  Phe Glu Pro Ser Ser  Asn Leu Gly
        1055                1060                1065

Pro Asn  Gln Asn Ser Ala Val  Ile Pro Ala Asn Ser  Leu Ser Ser
        1070                1075                1080
```

| Leu | Ile | Lys | Thr | Glu | Val | Asn | Gly | Phe | Val | His | Val | Ser | Pro | Gln |
|---|---|---|---|---|---|---|---|---|---|---|---|---|---|---|
| 1085 | | | | 1090 | | | | | 1095 | | | | | |

| Asp | Ser | Lys | Asp | Thr | Pro | Thr | Ser | His | Val | Pro | Ser | Gly | Pro | Leu |
|---|---|---|---|---|---|---|---|---|---|---|---|---|---|---|
| 1100 | | | | | 1105 | | | | | 1110 | | | | |

| Ser | Ser | Ser | Ala | Thr | Ser | Pro | Val | Leu | Leu | Pro | Ala | Leu | Pro | Arg |
|---|---|---|---|---|---|---|---|---|---|---|---|---|---|---|
| 1115 | | | | | 1120 | | | | | 1125 | | | | |

| Arg | Thr | Pro | Lys | Gln | His | Tyr | Cys | Asn | Thr | Cys | Gly | Lys | Thr | Phe |
|---|---|---|---|---|---|---|---|---|---|---|---|---|---|---|
| 1130 | | | | | 1135 | | | | | 1140 | | | | |

| Ser | Ser | Ser | Ser | Ala | Leu | Gln | Ile | His | Glu | Arg | Thr | His | Thr | Gly |
|---|---|---|---|---|---|---|---|---|---|---|---|---|---|---|
| 1145 | | | | | 1150 | | | | | 1155 | | | | |

| Glu | Lys | Pro | Phe | Ala | Cys | Thr | Ile | Cys | Gly | Arg | Ala | Phe | Thr | Thr |
|---|---|---|---|---|---|---|---|---|---|---|---|---|---|---|
| 1160 | | | | | 1165 | | | | | 1170 | | | | |

| Lys | Gly | Asn | Leu | Lys | Val | His | Met | Gly | Thr | His | Met | Trp | Asn | Ser |
|---|---|---|---|---|---|---|---|---|---|---|---|---|---|---|
| 1175 | | | | | 1180 | | | | | 1185 | | | | |

| Thr | Pro | Ala | Arg | Arg | Gly | Arg | Arg | Leu | Ser | Val | Asp | Gly | Pro | Met |
|---|---|---|---|---|---|---|---|---|---|---|---|---|---|---|
| 1190 | | | | | 1195 | | | | | 1200 | | | | |

| Thr | Phe | Leu | Gly | Gly | Asn | Pro | Val | Lys | Phe | Pro | Glu | Met | Phe | Gln |
|---|---|---|---|---|---|---|---|---|---|---|---|---|---|---|
| 1205 | | | | | 1210 | | | | | 1215 | | | | |

| Lys | Asp | Leu | Ala | Ala | Arg | Ser | Gly | Ser | Gly | Asp | Pro | Ser | Ser | Phe |
|---|---|---|---|---|---|---|---|---|---|---|---|---|---|---|
| 1220 | | | | | 1225 | | | | | 1230 | | | | |

| Trp | Asn | Gln | Tyr | Ala | Ala | Ala | Leu | Ser | Asn | Gly | Leu | Ala | Met | Lys |
|---|---|---|---|---|---|---|---|---|---|---|---|---|---|---|
| 1235 | | | | | 1240 | | | | | 1245 | | | | |

| Ala | Asn | Glu | Ile | Ser | Val | Ile | Gln | Asn | Gly | Gly | Ile | Pro | Pro | Ile |
|---|---|---|---|---|---|---|---|---|---|---|---|---|---|---|
| 1250 | | | | | 1255 | | | | | 1260 | | | | |

| Pro | Gly | Ser | Leu | Gly | Ser | Gly | Asn | Ser | Ser | Pro | Val | Ser | Gly | Leu |
|---|---|---|---|---|---|---|---|---|---|---|---|---|---|---|
| 1265 | | | | | 1270 | | | | | 1275 | | | | |

| Thr | Gly | Asn | Leu | Glu | Arg | Leu | Gln | Asn | Ser | Glu | Pro | Asn | Ala | Pro |
|---|---|---|---|---|---|---|---|---|---|---|---|---|---|---|
| 1280 | | | | | 1285 | | | | | 1290 | | | | |

| Leu | Ala | Gly | Leu | Glu | Lys | Met | Ala | Ser | Ser | Glu | Asn | Gly | Thr | Asn |
|---|---|---|---|---|---|---|---|---|---|---|---|---|---|---|
| 1295 | | | | | 1300 | | | | | 1305 | | | | |

| Phe | Arg | Phe | Thr | Arg | Phe | Val | Glu | Asp | Ser | Lys | Glu | Ile | Val | Thr |
|---|---|---|---|---|---|---|---|---|---|---|---|---|---|---|
| 1310 | | | | | 1315 | | | | | 1320 | | | | |

Ser

<210> SEQ ID NO 2
<211> LENGTH: 5143
<212> TYPE: DNA
<213> ORGANISM: Homo sapiens

<400> SEQUENCE: 2

```
ttattctgcc ccagctgatg tttgagccag catgtcgcgg aggaagcaag cgaagcctca      60
acatttccaa tccgaccccg aagtggcctc gctcccccgg cgagatggag acacagaaaa     120
gggtcaaccg agtcgcccta ctaagagcaa ggatgcccac gtctgtggcc ggtgctgtgc     180
cgagttcttt gaattatcag atcttctgct ccacaagaag aactgtacta aaaatcaatt     240
agttttaatc gtaaatgaaa atccagcctc cccacccgaa accttctccc ccagcccccc     300
tcctgataat cctgatgaac aaatgaatga cacagttaac aaaacagatc aagtggactg     360
cagcgacctt tcagaacaca acggacttga cagggaagag tccatggagg tggaggcccc     420
ggttgctaac aaaagcggca gcggcacttc cagcggcagc cacagcagta ccgccccaag     480
cagcagcagc agcagcagca gcagcagcgg cggcggcggc agctcctcca caggtacctc     540
agcgatcaca acctctctac ctcaactcgg ggacctgaca cactgggca acttctccgt     600
aatcaacagc aacgtcatca tcgagaacct ccagagcacc aaggtggcgg tggcccagtt     660
```

```
ctcccaggaa gcgaggtgcg gcggggcctc tggggcaag ctggccgtcc cagccctcat      720
ggaacaactc ctagctctgc agcagcagca gatccaccag ctgcaattga tcgaacagat     780
tcgtcaccaa atattgctgt tggcttctca gaatgcagac ttgccaacat cttctagtcc     840
ttctcaaggt actttacgaa catctgccaa ccccttgtcc acgctaagtt cccatttatc     900
tcagcagctg gcagcagcag ctggattggc acagagcctc gccagccaat ctgccagcat     960
tagtggtgtg aaacagctac ccccaatcca gctacctcag agcagttctg caacaccat    1020 cattccatcc aacagcggct cttctcccaa tatgaacata ttggcagcgg cagttaccac    1080
cccgtcctct gaaaagtgg cttcaagtgc tggggcctcc catgtcagca cccagcggt     1140 ctcatcatcg tcctcaccag cttttgcaat aagcagttta ttaagtcctg cgtctaatcc    1200
acttctacct cagcaagcct ccgctaactc ggttttcccc agcccttgc ccaacatcgg    1260 aacaactgca gaggatttaa actccttgtc tgccttggcc cagcaaagaa aaagcaagcc    1320
accaaatgtc actgcctttg aagcgaaaag tacttccgat gaggcattct tcaaacacaa    1380
gtgcaggttc tgcgcgaagg tctttgggag tgacagtgcc ttgcagatcc acttgcgttc    1440
ccataccgga gagaggccat tcaagtgcaa catctgcggg aacaggttct ccaccaaggg    1500
gaatctgaaa gtccactttc agcgccacaa agagaaatac cctcatatcc agatgaaccc    1560
ctatcctgtg cctgagcatt tggacaatat ccccacgagt actggcatcc catatggcat    1620
gtccatccct ccagagaagc cagtcaccag ctggctagac accaaaccag tcctgcctac    1680
tctgaccact tcagtcggcc tgccgttgcc cccaacccte ccaagcctca taccttcat    1740 caagacggaa gagccagccc ccatccccat cagccattct gccaccagcc ccccaggctc    1800
agtcaaaagt gactccgggg gccctgagtc agccacaaga aacctaggtg ggctcccaga    1860
ggaagccgaa gggtccactc tgccaccctc tggtggcaaa agcgaagaga gtggcatggt    1920
caccaactca gtcccgacgg cgagcagtag cgtcctgagc tccccagcgg cagactgcgg    1980
ccccgcgggc agtgccacca ccttccaccaa cccttttgttg ccgctcatgt ccgagcagtt   2040
caaggccaag tttccttttg ggggactcct ggactcagct caggcatcag agacgtccaa    2100
gcttcagcaa ctggtagaaa acattgacaa gaaggccact gaccccaatg agtgcatcat    2160
ctgccaccgg gttctcagct gccagagcgc cttgaaaatg cactacagga cacacactgg    2220
ggagaggccc tttaagtgta agatctgtgg ccgggctttc accacgaaag ggaatcttaa    2280
aacccactac agtgtccatc gtgctatgcc cccgctcaga gtccagcatt cctgccccat    2340
ctgccagaag aagttcacga acgctgtggt cctgcagcag cacatccgaa tgcatatggg    2400
aggccagatc cccaacaccc cagtccccga cagctactct gagtccatgg agtctgacac    2460
aggttccttt gatgagaaaa attttgatga cctagacaac ttctctgatg aaaacatgga    2520
agactgtcct gagggcagca tccctgatac acctaagtct gcagacgcct cccaagacag    2580
cttatcctct tcgcctttgc ccctcgagat gtcgagcatc gctgctttgg aaaatcagat    2640
gaagatgatc aatgctggcc tggcagagca gctacaggcc agcctgaagt cagtggagaa    2700
tgggtccatc gagggggatg tcctgaccaa tgattcatcc tcagtgggtg gtgacatgga    2760
aagccaaagt gctggcagcc cagcatctc agagtctacc tcttccatgc aggctctgtc    2820
cccgtccaac agcacgcagg agttccacaa gtcacccagc attgaggaga accacagag    2880 agcggtccca agcgagtttg ccaatggttt gtctcccacc ccagtgaatg gtggggcttt    2940
ggatttgaca tctagtcacg cagagaaaat catcaaagaa gattctttgg ggatcctctt    3000
```

```
cccttttaga gaccggggta aatttaaaaa cactgcttgt gacatttgtg gcaaaacatt    3060
tgcttgtcag agtgccttgg acattcacta tagaagtcat accaaagaga gaccatttat    3120
ttgcacagtt tgcaatcgtg gcttttccac aaagggtaat ttgaagcagc acatgttgac    3180
acatcagatg cgagatctgc catcccagct ctttgagccc agttccaacc ttggccccaa    3240
tcagaactca gcggtgattc ccgccaactc gttgtcatct ctcatcaaga cagaggtcaa    3300
cggcttcgtg catgtttctc ctcaggacag taaggacacc cccaccagtc acgtcccgtc    3360
tgggcctctg tcttcctctg ccacatcccc agttctgctc cctgctctgc ccaggagaac    3420
tcccaagcag cactactgca acacatgtgg caaaaccttc tcctcatcga gtgccctgca    3480
gattcacgag agaactcaca ctggagagaa acccttgct tgcactattt gtggaagagc     3540
tttcacgact aaaggcaatc ttaaggtaca catgggcact cacatgtgga atagcacccc    3600
tgcacgacgg ggtcggcggc tctctgtgga tggccccatg acatttctag gaggcaatcc    3660
cgtcaagttc ccagaaatgt tccagaagga tttggcggca agatcaggaa gtggggatcc    3720
ttccagcttg tggaatcagt atgcagcagc gctctccaac gggctggcga tgaaggccaa    3780
cgagatctcc gtcattcaga acggtggcat ccctccaatt cctggaagcc tcggcagtgg    3840
gaacagctca cctgttagtg ggctgacggg aaacctggag aggctccaga actcagagcc    3900
caatgctccc ctggccggcc tggagaaaat ggcaagcagt gagaacggaa ccaacttccg    3960
cttcacccgc ttcgtggagg acagcaagga gatcgtcacg agttaaagca gctcgggctg    4020
gagacatagc attcattcct gttcagaatg cgacctatgg tggcctccta ctccttgccc    4080
cccaccccgc cccgcccctt ccttctgttc cccagatcta tgaactacaa cattatgaag    4140
acattctttt gtaccttgtt caactttaga gttctaagaa agcttattta ttagcgatat    4200
aaccttgctt tgcaaacaga atgcaagcgt taactttggt cttctgtatt ttggactaaa    4260
tactaattga ctagagtgct gtaaacttgc tgtaacattt atggcaattg caagttgccc    4320
tgctaggcag ttgtaatctg gcattaactt attttctata tccagtttaa tatgaatctg    4380
gtgttgatgc aatgcctcag tgatgcatta gatctctaat aaagtctgta tatacatgta    4440
cactttgatc ctgctggaaa attttatcag caaacacatt gtctaatctt tcaaaacaga    4500
tttaaggaaa ggactgaaag tacagactga acagtgtggt tctttgaaag gtttggtttt    4560
ttaatttta ttctaaaatt caacctttt tttgtcgat ttaaccattt ccattttgaa       4620
ctgctatttg tattgtgctt tttacttgag tcgtcttcaa tgttaataag tttctgtaca    4680
gtaataagca cgcagaattc tttagagaaa aagaaaacaa gcgttgtttt ggtagttgaa    4740
actgagacgt aacattttgc cttgtaggta tattcacgat agaaaatgtg tgctggaatt    4800
tcacaatgct gctaagtata gcatcttgaa caaccttcag tggagaaaat gtagatgctc    4860
ttgtatatac aataagaaat atcactttca ttcaaatgta catatgttcc ttacaagagc    4920
aaatgcttct tcttgatcaa gagagcaggt atagtgtttg tttattttgt cttaggtatg    4980
gaagaaaaaa attggactgt tacatgcact ttccttggaaa gttgaaagga agggggggt    5040
ccaatttctt taacatttaa tacttactaa caacagagat actgtaattt tactcaagta    5100
atcaaataca tttttttgc aacagataaa acaaaatact gtg                       5143
```

<210> SEQ ID NO 3
<211> LENGTH: 17
<212> TYPE: DNA
<213> ORGANISM: Artificial sequence
<220> FEATURE:
<223> OTHER INFORMATION: Synthetic oligonucleotide -continued

<400> SEQUENCE: 3
tgatgtagcc agcatgt                                                   17

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
aaagaattca gcgcagcac                                                 19

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
ccaagagtaa agcggatgag a                                              21

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
agtaagcagt gcccaactcg                                                20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tgggccttcg cttactaaag                                                20

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
acagcagtgg cagctgaag                                                 19

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
agcagcctca gcagctacc                                                 19

<210> SEQ ID NO 10

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
aagaactcgg cacagcattt                                              20
```